(12) United States Patent
Clague et al.

(10) Patent No.: US 10,105,225 B2
(45) Date of Patent: Oct. 23, 2018

(54) DEVICES, SYSTEMS AND METHODS FOR TISSUE APPROXIMATION, INCLUDING APPROXIMATING MITRAL VALVE LEAFLETS

(71) Applicant: Medtronic, Inc., Minneapolis, MN (US)

(72) Inventors: Cynthia Clague, Minnetonka, MN (US); James Keogh, Maplewood, MN (US); Ana Menk, St. Paul, MN (US); Paul Rothstein, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 248 days.

(21) Appl. No.: 14/882,732

(22) Filed: Oct. 14, 2015

(65) Prior Publication Data

US 2016/0113762 A1    Apr. 28, 2016

Related U.S. Application Data

(60) Provisional application No. 62/066,968, filed on Oct. 22, 2014.

(51) Int. Cl.
*A61F 2/24*      (2006.01)
*A61B 17/064*    (2006.01)
(Continued)

(52) U.S. Cl.
CPC ........ *A61F 2/246* (2013.01); *A61B 17/00234* (2013.01); *A61B 17/068* (2013.01); *A61B 17/0643* (2013.01); *A61B 17/122* (2013.01); *A61F 2/2463* (2013.01); *A61F 2/2466* (2013.01); *A61B 17/1285* (2013.01); *A61B 2017/00243* (2013.01);
(Continued)

(58) Field of Classification Search
CPC ...... A61F 2/246; A61F 2/2442; A61F 2/2451; A61F 2/2454; A61B 17/00234
See application file for complete search history.

(56) References Cited

U.S. PATENT DOCUMENTS 6,926,715 B1   8/2005  Hauck et al.
7,285,087 B2  10/2007  Moaddeb et al.
(Continued)

FOREIGN PATENT DOCUMENTS

EP    1674040      6/2006
WO    WO2007016122  2/2007

OTHER PUBLICATIONS

PCT/US2015/056259, The International Search Report and the Written Opinion of the International Searching Authority, dated Jan. 20, 2016.

*Primary Examiner* — Diane Yabut
(74) *Attorney, Agent, or Firm* — Dicke, Billig & Czaja, PLLC

(57) ABSTRACT

Systems and methods for approximating tissue segments, such as mitral valve leaflets, on a minimally invasive basis. The system includes first and second approximation devices each including a magnetic component and an attachment mechanism. Each device is connected to a target tissue segment by the corresponding attachment mechanism. Upon deployment at a target site, the tissue approximation devices are magnetically attracted to one another, approximating the tissue segments and maintaining the tissue segments in the approximated state.

9 Claims, 22 Drawing Sheets

(51) Int. Cl.
  *A61B 17/068*  (2006.01)
  *A61B 17/122*  (2006.01)
  *A61B 17/128*  (2006.01)
  *A61B 17/00*  (2006.01)

(52) U.S. Cl.
  CPC .............. *A61B 2017/00349* (2013.01); *A61B 2017/00477* (2013.01); *A61B 2017/00876* (2013.01); *A61B 2017/0649* (2013.01); *A61F 2210/009* (2013.01); *A61F 2220/0016* (2013.01)

(56) References Cited

U.S. PATENT DOCUMENTS

| | | |
|---|---|---|
| 7,357,815 B2 | 4/2008 | Shaoulian et al. |
| 7,377,941 B2 | 5/2008 | Rhee et al. |
| 7,396,364 B2 | 7/2008 | Maoddeb et al. |
| 7,402,134 B2 | 7/2008 | Maoddeb et al. |
| 7,431,726 B2 | 10/2008 | Spence et al. |
| 7,510,577 B2 | 3/2009 | Maoddeb et al. |
| 8,784,482 B2 | 7/2014 | Rahdert |
| 2005/0216039 A1 | 9/2005 | Lederman |
| 2006/0015003 A1 | 1/2006 | Moaddes et al. |
| 2006/0030867 A1 | 2/2006 | Zadno |
| 2006/0229708 A1* | 10/2006 | Powell ............. A61B 17/00234 623/1.24 |
| 2007/0080188 A1 | 4/2007 | Spence et al. |
| 2008/0140188 A1* | 6/2008 | Rahdert ........... A61B 17/00234 623/2.1 |
| 2012/0022557 A1 | 1/2012 | Cabiri et al. |
| 2013/0282059 A1 | 10/2013 | Ketai et al. |
| 2014/0114403 A1* | 4/2014 | Dale ................ A61B 17/00234 623/2.11 |

\* cited by examiner

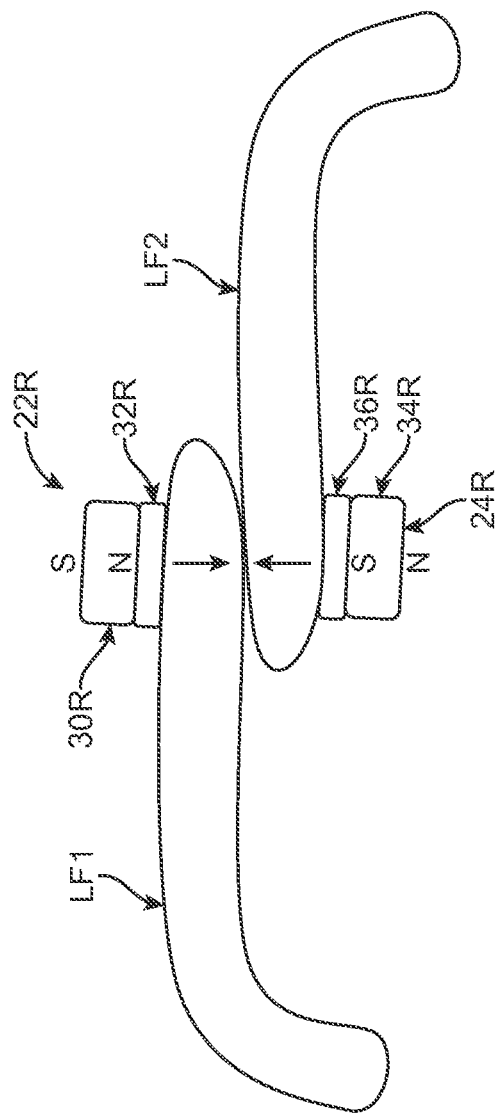

DEVICES, SYSTEMS AND METHODS FOR TISSUE APPROXIMATION, INCLUDING APPROXIMATING MITRAL VALVE LEAFLETS

CROSS REFERENCE TO RELATED APPLICATIONS

This Non-Provisional patent application claims the benefit of the filing date of U.S. Provisional Patent Application Ser. No. 62/066,968, filed Oct. 22, 2014, entitled "Devices, Systems and Methods for Tissue Approximation, Including Approximating Mitral Valve Leaflets," which is herein incorporated by reference.

BACKGROUND

The present disclosure relates to devices, systems and methods for approximating tissue. More particularly, it relates to endovascular, percutaneous or minimally invasive devices, systems and methods for approximating tissue at various anatomical regions, for example in repairing a cardiac valve (such as the mitral valve) via leaflet edge-to-edge approximation or attachment.

The heart is a four-chambered pump that moves blood efficiently through the vascular system. Blood enters the heart through the vena cava and flows into the right atrium. From the right atrium, blood flows through the tricuspid valve and into the right ventricle, which then contracts and forces blood through the pulmonic valve and into the lungs. Oxygenated blood returns from the lungs and enters the heart through the left atrium and passes through the mitral valve and into the left ventricle. The left ventricle contracts and pumps blood through the aortic valve, into the aorta, and to the vascular system.

The mitral valve consists of two leaflets (anterior and posterior) attached to a fibrous ring or annulus. The leaflets each form a free edge opposite the annulus. The free edges of the leaflets are secured to lower portions of the left ventricle through chordae tendineae (or "chordae") that include a plurality of branching tendons secured over the lower surfaces of each of the valve leaflets. The chordae are further attached to papillary muscles that extend upwardly from the lower portions of the left ventricle and interventricular septum.

In a healthy heart, the free edges of the mitral valve leaflets close against one another (or coapt) during contraction of the left ventricle to prevent oxygenated blood from flowing back into the left atrium. In this way, the oxygenated blood is pumped into the aorta through the aortic valve. However, due to cardiac disease, valve defects, or other reasons, the leaflets may be caused to remain partially spaced or open during ventricular contraction (e.g., leaflet prolapse) and thus allow regurgitation of blood into the left atrium. This results in reduced ejection volume from the left ventricle, causing the left ventricle to compensate with a larger stroke volume. Eventually, the increased work load results in dilation and hypertrophy of the left ventricle, enlarging and distorting the shape of the mitral valve. Mitral valve regurgitation in an increasingly common cardiac condition that can quickly lead to heart failure, dangerous arrhythmias, and other serious complications.

It is common medical practice to treat mitral valve regurgitation by either valve replacement or repair. Valve replacement conventionally entails an open-heart surgical procedure in which the patient's mitral valve is removed and replaced with an artificial valve. This is a complex, invasive surgical procedure with the potential for many complications and a long recovery.

Mitral valve repair includes a variety of procedures to repair or reshape the leaflets and/or the annulus to improve closure of the valve during ventricular contraction. If the mitral valve annulus has become distended, a frequent repair procedure involves implanting an annuloplasty ring or band on the mitral valve annulus. Another approach for treating mitral valve regurgitation requires a flexible elongated device that is inserted into the coronary sinus and adapts to the shape of the coronary sinus. The device then undergoes a change that causes it to assume a reduced radius of curvature, and as a result, causes the radius of curvature of the coronary sinus and the circumference of the mitral annulus to be reduced. A more recent technique for mitral valve repair entails the suturing or fastening or approximating of segments of the opposed valve leaflet free edges together, and is referred to as a "bow-tie" or "edge-to-edge" technique. While all of these techniques can be very effective, they usually rely on open heart surgery where the patient's chest is opened, typically via sternotomy, and the patient placed on cardiopulmonary bypass. While some percutaneous or transcatheter mitral valve repair procedures have been contemplated premised upon the edge-to-edge technique, the confined nature of the native mitral valve anatomy renders capturing and securing of the leaflets with a single clip or device exceedingly difficult. Capturing a first leaflet may be relatively straightforward, but then the anchor on that leaflet constrains grabbing the other leaflet.

Procedures at other valves and other anatomical regions also seek to achieve tissue approximation on a minimally invasive basis, and are faced with many of the same obstacles described above with respect to the mitral valve.

In light of the above, a need exists for devices, systems and methods for minimally invasive tissue approximation at various anatomical regions such as in repairing a mitral valve in the treatment of mitral valve regurgitation.

SUMMARY

Some aspects of the present disclosure relate to systems and methods for approximating tissue segments, such as mitral valve leaflets, on a minimally invasive basis. The system includes first and second approximation devices each including a magnetic component and an attachment mechanism. Each device is connected to a target tissue segment by the corresponding attachment mechanism. Upon deployment at a target site, the tissue approximation devices are magnetically attracted to one another, approximating the tissue segments and maintaining the tissue segments in the approximated state.

BRIEF DESCRIPTION OF THE DRAWINGS

FIG. 20 is a simplified side view of a portion of another tissue approximation system in accordance with principles of the present disclosure as applied to tissue segments.

DETAILED DESCRIPTION

Figure 1A:
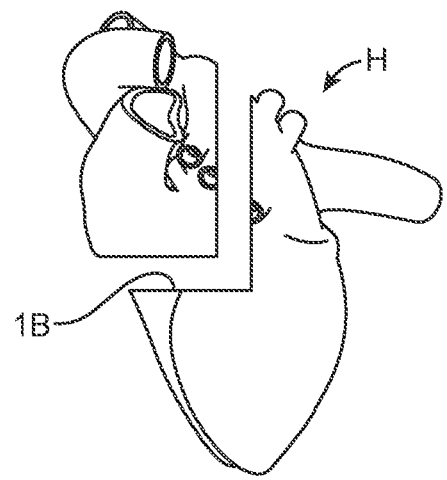
FIG. 1A is a simplified anterior view of a human heart.
Figure 1B:
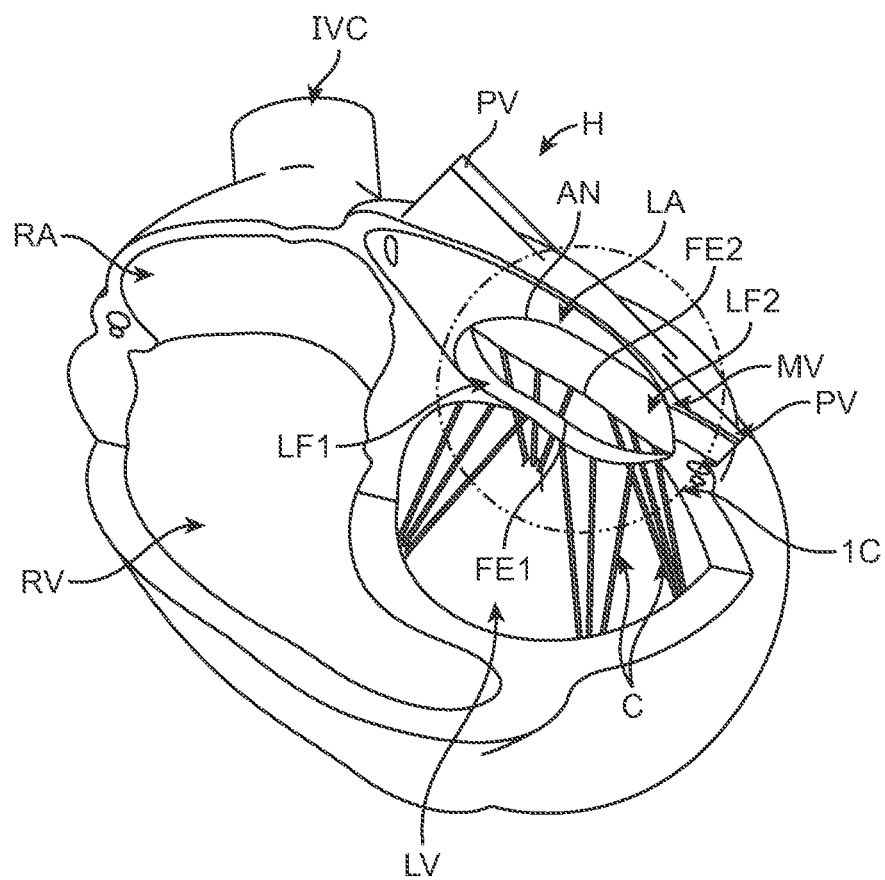
FIG. 1B is a partial cross-sectional view of the heart of FIG. 1A along section line 1B.
Figure 1C:
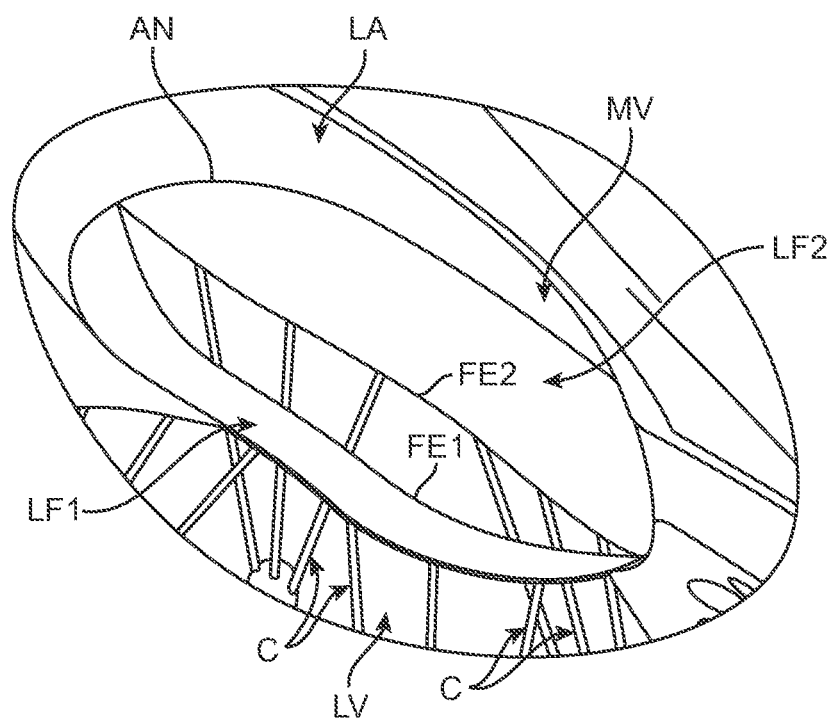
FIG. 1C is an enlarged perspective view of a portion of the heart of FIG. 1B, illustrating a mitral valve in an open arrangement.
Figure 1D:
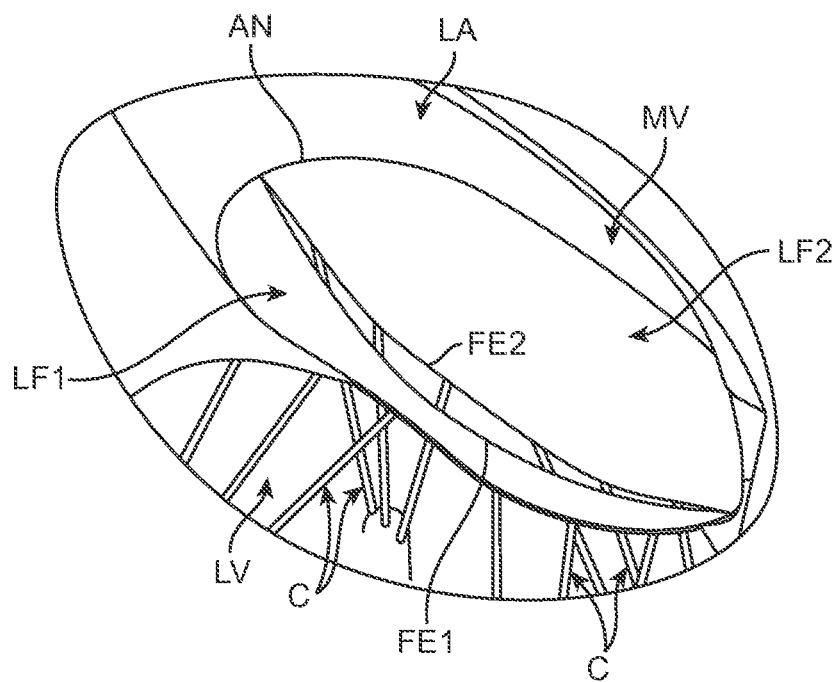
FIG. 1D is an enlarged perspective view of a portion of the heart of FIG. 1B in systole and illustrating a defective mitral valve.

Aspects of the present disclosure relate to devices, systems and methods for approximating tissue on a minimally invasive basis. In some embodiments, the devices of the present disclosure incorporate two (or more) complementary magnetic elements and are useful in approximating and maintaining tissue of the mitral valve (e.g., the opposing leaflets) as described below. The present disclosure is in no way limited to mitral valve-related repair or procedures, and the systems and methods of the present disclosure are equally useful at a multitude of other anatomical regions. Relative to the non-limiting uses in connection with the mitral valve, anatomy of a normal heart H is shown in FIGS. 1A-1C. The mitral valve MV is located between the left atrium LA and the left ventricle LV. Also shown are the inferior vena cava IVC, right atrium RA, right ventricle RV, and pulmonary veins PVs. The mitral valve MV includes first and second leaflets LF1, LF2 extending from a valve annulus AN (referenced generally). Each of the leaflets LF1, LF2 terminates at a free edge FE1, FE2, respectively. The free edges FE1, FE2 are secured to lower portions of the left ventricle LV through chordae C. When the heart H is in systole, backflow of blood or "regurgitation" through the mitral valve MV is prevented by the free edges FE1, FE2 of the leaflets LF1, LF2 overlapping one another or coapting. Disease or other anatomical deficiencies can prevent coaptation from occurring as shown in FIG. 1D, resulting in mitral valve regurgitation. Systems and methods of the present disclosure can be used to treat this malady, for example by approximating and maintaining the leaflets LF1, LF2 (e.g., in a region of the corresponding free edges FE1, FE2). Many of the systems of the present disclosure are illustrated and described below as applied to tissue segments generally corresponding in shape to the mitral valve leaflets LF1, LF2 for ease of understanding. However, because the systems and methods of the present disclosure are equally useful at many other anatomical target sites with different tissue structures, the descriptions below more accurately and inclusively refer to the leaflets LF1, LF2 as "tissue segments".

Figure 2A:
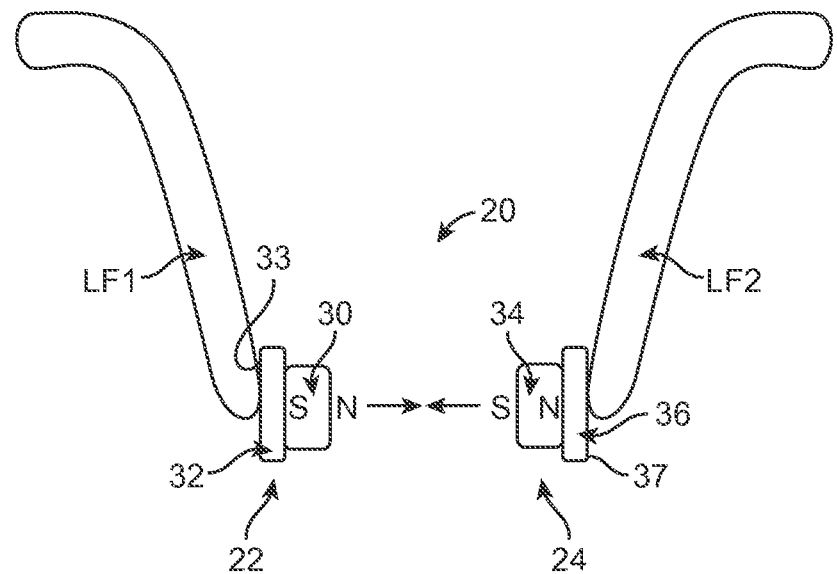
FIG. 2A is a simplified view of a tissue approximation system in accordance with principles of the present disclosure and as initially applied to two tissue segments, such as two mitral valve leaflets.

With the above explanations in mind, general aspects of the present disclosure are reflected by a tissue approximation system 20 in FIG. 2A as initially applied (e.g., attached) to the opposing tissue segments LF1, LF2 (such as leaflets or any other tissue segments for which approximation is desired). The system 20 includes first and second approximation devices 22, 24. The first device 22 includes at least one magnetic component 30 and an attachment mechanism 32. The second device 24 can be highly similar to the first device 22, optionally identical, and also includes at least one magnetic component 34 and an attachment mechanism 36. In general terms, the attachment mechanisms 32, 36 can assume a variety of forms and are each configured to couple or otherwise spatially affix the corresponding magnetic component 30, 34 relative to a respective one of the tissue segments LF1, LF2. Upon connection to the tissue segments LF1, LF2, the magnetic components 30, 34 are arranged in a complementary fashion such that the associated magnetic field(s) attracts the magnetic components 30, 34 (and thus the tissue segments LF1, LF2) toward one another (represented by arrows in FIG. 2A). Due to this magnetic force or attraction, the system 20 approximates the leaflets LF1, LF2 as reflected by FIG. 2B, and maintains the so-approximated leaflets LF1, LF2 in the approximated state.

Various embodiments of tissue approximation systems in accordance with principles of the present disclosure are described below, including examples of useful attachment mechanism configurations. The magnetic components 30, 34 can assume a variety of forms appropriate for effectuating desired tissue approximation. The following descriptions of the magnetic components 30, 34 apply equally to all embodiments of the present disclosure.

In most general terms, at least one of the magnetic components 30, 34 includes at least one magnetized element (e.g., a permanent magnet or electromagnet that generates a magnetic field). The magnetized element can be formatted or provided in any manner known to those of ordinary skill, and non-limiting examples of useful materials that can be magnetized to serve as the magnetized element include neodymium-iron-boron (NdFeB), samarium-cobalt (SmCo), and aluminum-nickel-cobalt (AlNiCo). In some embodiments, both of the magnetic components 30, 34 include at least one magnetized element, with the approximation devices 22, 24 being configured such that upon intended assembly to the respective tissue segment LF1, LF2, the magnetized elements are naturally arranged in a complementary fashion whereby opposite pole "sides" of the magnetized elements face one another (and thus magnetically attract one another). For example, FIG. 2A reflects the magnetic components 30, 34 as each establishing north and south poles ("N" and "S") via one or more magnetized elements (not shown). Once coupled to the respective tissue segment LF1, LF2, opposite magnetic pole sides of the magnetic components 30, 34 face one another (e.g., the "north" pole of the magnetic component 30 of the first approximation device 22 faces the "south" pole of the magnetic component 34 of the second approximation device 24). In other embodiments, only one of the magnetic components 30, 34 includes a magnetized element, with the other magnetic component 30, 34 including a non-magnetized ferromagnetic metal (or other non-magnetized material that is affected by, and attracted to, the magnetic field generated by the magnetized element of the other magnetic component 30, 34). In other words, the term "magnetic component" is in reference to a component affected by a magnetic field, and is not limited to or does not require the inclusion of a magnetized element.

The magnetic components 30, 34 can be identical or different from one another. The magnetic components 30, 34 can each comprise one or more elements or materials having magnetic, ferromagnetic and/or electromagnetic properties. The magnetic components 30, 34 may each comprise one or more elements or materials that are magnetic or that are capable of being magnetized. The magnetic components 30, 34 can each comprise one or more magnetic and non-magnetic elements or materials arranged in a laminated or layered structure. For example, a laminated structure useful for one or both of the magnetic components 30, 34 can comprise a layer of material capable of producing a magnetic field disposed between two layers of material also capable of producing a magnetic field, or, alternatively, ferromagnetic or non-ferromagnetic, and/or may comprise a metal, polymer, ceramic, etc. In one non-limiting embodiment, one or both of the magnetic components 30, 34 can comprise a middle layer of NeFeB (Neodymium Iron Boron—magnetic) and two outer layers of stainless steel (non-magnetic). The outer layers can be bonded to the middle layer by a suitable adhesive or coating for example (e.g., parylene polymer or parylene/gold coated to one or more layers of magnetic or magnetized material). In other embodiments, one or both of the magnetic components 30, 34 can comprise two outer layers of a magnetic material surrounding a middle layer that is either magnetic or non-magnetic.

A benefit of the optional laminated or layered construction is that it allows the thickness of the magnetic layer to be reduced since one or more additional layers can be formed of one or more materials that may provide the layered assembly with the necessary strength that the magnetic layer alone may not provide. Additional optional benefits include biocompatibility, corrosion resistance, possibly better tissue interface and integration, etc.

The specific size and shape of the magnetic components 30, 34 can be varied. For example, a thickness and/or width of the magnetic components 30, 34 (or magnetic element(s) provided with each of the magnetic components 30, 34) can vary along all or part of the magnetic component 30, 34. The amount of magnetic force exerted can be tailored as desired, and is a function of various factors such as the materials used, size, and number of magnetized elements provided. As a point of reference, different end-use applications may entail different magnetic force characteristics or ranges. In general terms, the selected magnetic field(s) should provide sufficient attractive force so that the tissue approximation devices 22, 24 remain securely magnetically coupled under the expected conditions at the anatomical region to which the system 20 is installed or implanted. For example, where the system 20 is deployed to approximate and maintain the opposing leaflets LF1, LF2 of the mitral valve, the magnetic force associated with the system 20 is selected so as to maintain a secure magnetic coupling throughout the entire cardiac cycle. The selected magnetic force optionally accounts for other anatomical concerns, for example is not so forceful so as to necrose tissue "squeezed" between the magnetic components 30, 34.

The attachment mechanisms 32, 36 can be identical or different, and optional embodiments are described below. In more general terms, in some embodiments one or both of the attachment mechanisms 32, 36 can comprise, for example, one or more clips, clamps, fasteners, rivets, staples, sutures, magnets, glues and a combination thereof such that the attachment mechanism can be secured to tissue. One of more surfaces of one or both of the attachment mechanisms 32, 36 can be coated, treated and/or comprises mechanical projections to enhance engagement with tissue. Further, one or more surfaces of one or both of the attachment mechanisms 32, 36 can have at least one friction-enhancing feature schematically represented as reference numerals 33, 37, that engages the target tissue, such as a prong, winding, band, barb, bump, groove, opening, channel, surface roughening, sintering, high friction pad, covering, coating and combinations thereof.

The particular construction of each of the attachment mechanisms 32, 36 is selected to remain securely coupled to the corresponding tissue segment LF1, LF2 under the expected conditions at the anatomical region to which the system 20 is installed or implanted. For example, where the system 20 is deployed to approximate and maintain the opposing leaflets LF1, LF2 of the mitral valve, the fastening mechanism or technique embodied by the attachment devices 32, 36 is selected so as to maintain a secure fastening to the corresponding leaflet LF1, LF2 throughout the entire cardiac cycle. The selected fastening mechanism or technique optionally accounts for other anatomical concerns, such as minimizing trauma to the fastened tissue segment. For example, the attachment mechanisms 32, 36 can be flexible so as to deflect to some degree in response to forces against the tissue segment engaged thereby to reduce the chance that the tissue segment will tear or bruise in response to such forces.

As implicated above, one or more surfaces of one or more components of one or both of the approximation devices 22, 24 can be coated or treated (e.g., an entirety of the approximation device 22, 24 can be coated or treated). Example materials that may be used in one or more coatings or treatments include gold, platinum, titanium, nitride, parylene, silicone, urethane, epoxy, Teflon, and polypropylene. In related embodiments, it may be desirable to promote tissue ingrowth around one or both of the approximation devices 22, 24 via a coating, covering or treatment selected to promote tissue growth. In one embodiment, a biocompatible fabric cover is positioned over one or more surfaces of one or both of the approximation devices 22, 24 (e.g., over a surface otherwise intended to directly contact tissue upon final installation). The cover may optionally be impregnated or coated with various therapeutic agents, including tissue growth promoters, antibiotics, anti-clotting, blood thinning, and other agents. Alternatively or in addition, some or all of the covering can be comprised of a bioerodable, biodegradable or bioabsorbable material so that it may degrade or be absorbed by the body. Other coatings are also envisioned, such as a manufactured tissue coating, ECM matrix, cellularized tissue matrix, etc.

In some embodiments, the covering may assist in grasping the tissue and may later provide a surface for tissue ingrowth. Ingrowth of the surrounding tissues (e.g., valve leaflets) provides stability to the approximation device 22, 24 as it is further anchored in place and may cover the approximation device 22, 24 with native tissue over time, thus reducing the possibility of immunologic reactions. The optional covering may be comprised of any biocompatible material, such as polyethylene terephthalate, polyester, cotton, polyurethane, expanded polytetrafluoroethylene (ePTFE), silicone, or various polymers or fibers and have any suitable format such as fabric, mesh, textured weave, felt, looped, porous structure, etc.

Where provided, the covering optionally has a low profile so as to not interfere with delivery through an introducer catheter or with grasping target tissue. The covering may alternatively be comprised of a polymer or other suitable materials dipped, sprayed, coated or otherwise bonded or adhered to the surface(s) of the approximation device 22, 24. Optionally, the polymer coating may include or define pores or contours to assist in grasping targeted tissue and/or promote tissue ingrowth. Moreover, any of the optional coverings of the present disclosure can optionally include drugs, antibiotics, anti-thrombosis agents, or anti-platelet agents such as heparin, Coumadin® (Warfarin sodium), to name but a few. These agents may, for example, be impregnated in or coated on the coverings. These agents may then be delivered to the tissue engaged by the approximation device 22, 24, to surrounding tissues and/or the bloodstream for therapeutic effects.

Figure 2B:
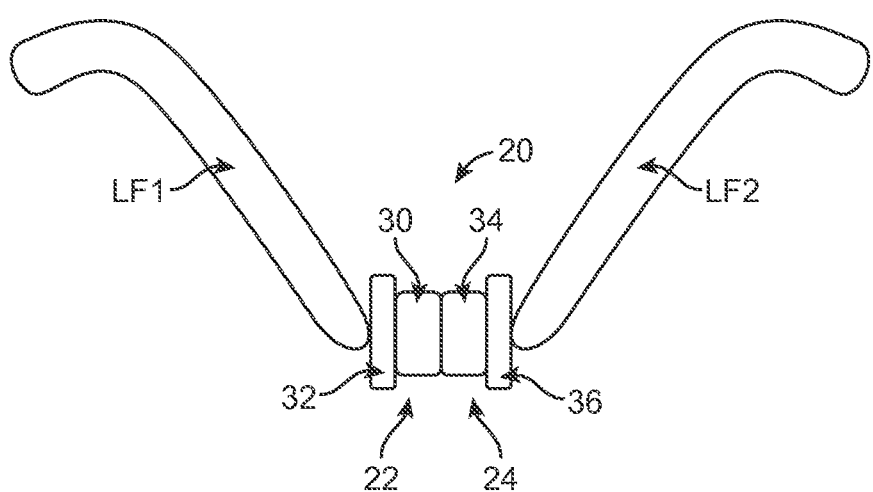
FIG. 2B is a simplified view of the system of FIG. 2A having directed the tissue segments to an approximated state.

Any of the described features herein can be incorporated into or utilized with any of the exemplary tissue approximation systems described below in accordance with principles of the present disclosure. As a point of reference, in the examples below, features common with the general explanations provided in conjunction with the system 20 of FIGS. 2A and 2B are identified by a common element number followed by a suffix indicative of a particular embodiment.

Figure 3A:
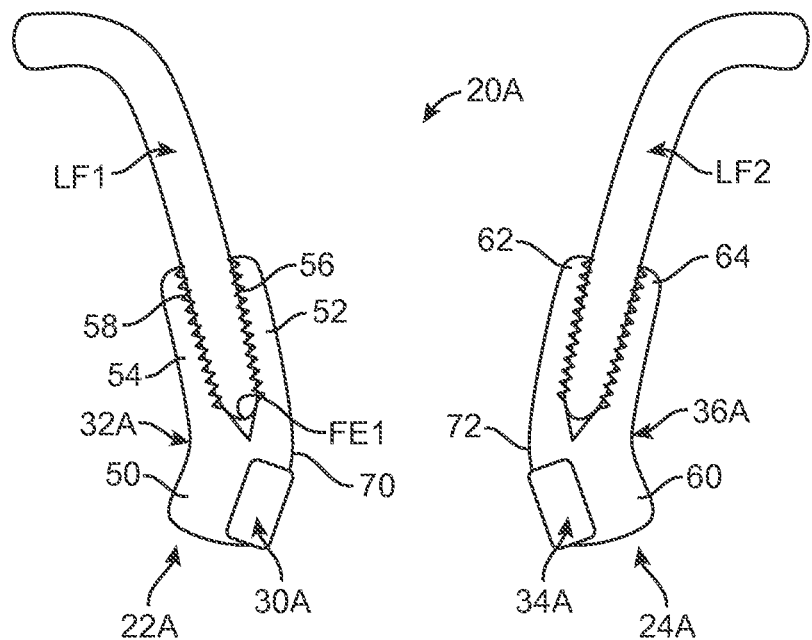
FIG. 3A is a simplified side view of another tissue approximation system in accordance with principles of the present disclosure and as initially applied to two tissue segments.

For example, another embodiment tissue approximation system 20A in accordance with principles of the present disclosure is shown in FIG. 3A and includes first and second approximation devices 22A, 24A. The first approximation device 22A includes at least one magnetic component 30A and an attachment mechanism 32A. The second approximation device 24A similarly includes at least one magnetic component 34A and an attachment mechanism 36A. The magnetic components 30A, 34A may or may not be identical, and can assume any of the forms described herein. With the embodiment of FIG. 3A, the attachment mechanisms 32A, 36A are highly similar, optionally identical, and include or comprise a clamping structure. For example, the attachment mechanism 32A of the first approximation device 22A includes a base 50 and opposing jaws 52, 54. The opposing jaws 52, 54 each optionally form a toothed or roughened surface 56, 58 and are maintained by and extend from the base 50 such that the jaws 52, 54 can pivot relative to one another. Further, the attachment mechanism 32A is configured such that the jaws 52, 54 are biased toward a closed position in which the toothed surfaces 56, 58 are in contact with each other (e.g., via a spring (not shown)). With this construction, the jaws 52, 54 can be temporarily forced to an opened position for placement over the tissue segment LF1 (e.g., placed over the free edge FE1) and upon release of the expansion force, self-revert back toward the closed position so as to achieved a clamped attachment to the tissue segment LF1. The attachment mechanism 36A of the second approximation device 24A can similarly include a base 60 and opposing, biased jaws 62, 64.

Figure 3B:
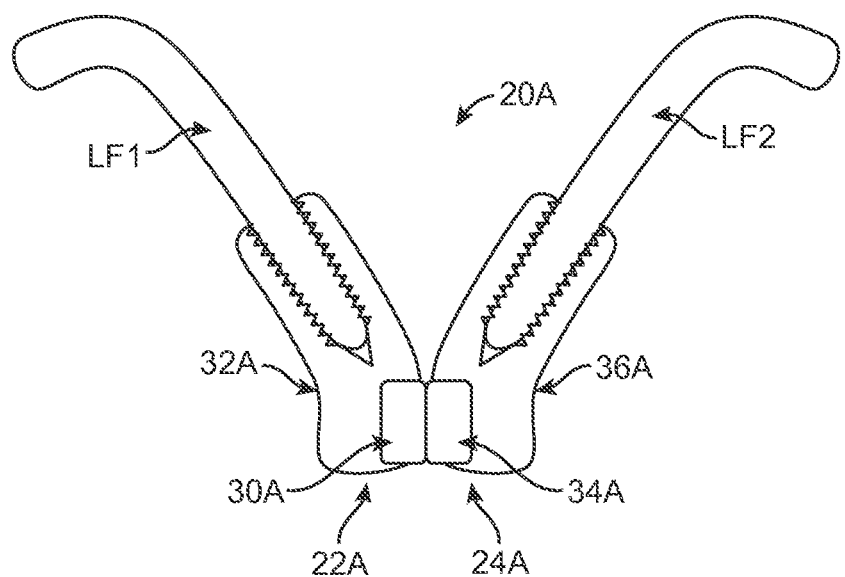
FIG. 3B is a simplified side view of the system of FIG. 3A having directed the tissue segments to an approximated state.

The magnetic component 30A, 34A is mounted or carried by the corresponding attachment mechanism 32A, 36A in a manner promoting a desired spatial arrangement upon connection to the respective tissue segment LF1, LF2. For example, a shape and operation of the attachment mechanism 32A naturally establishes an interior face 70 along the base 50 at the intended target site (e.g., with the exemplary embodiment in which the first approximation device 22A is fastened to the first mitral valve leaflet LF1, the interior face 70 of the base 50 naturally faces the second leaflet LF2). The magnetic component 30A can be carried by the base 50 at the interior face 70. The magnetic component 34A of the second approximation device 24A is similarly carried at an interior face 72 of the base 60. Thus, once applied at the intended target site, the magnetic components 30A, 34A are arranged to "face" one another; in related embodiments in which the magnetic components 30A, 34A each include one or more magnetized elements, the spatial arrangement established by the approximation devices 22A, 24A upon coupling to the respective tissue segments LF1, LF2 (in an expected manner) provides the complementary magnet pole arrangement as described above. Regardless, upon connection to the respective tissue segments LF1, LF2, the approximation devices 22A, 24A transition to the approximated state of FIG. 3B due to the magnetic force(s) described above, and maintain a position of the so-approximated tissue segments LF1, LF2.

Figure 4A:
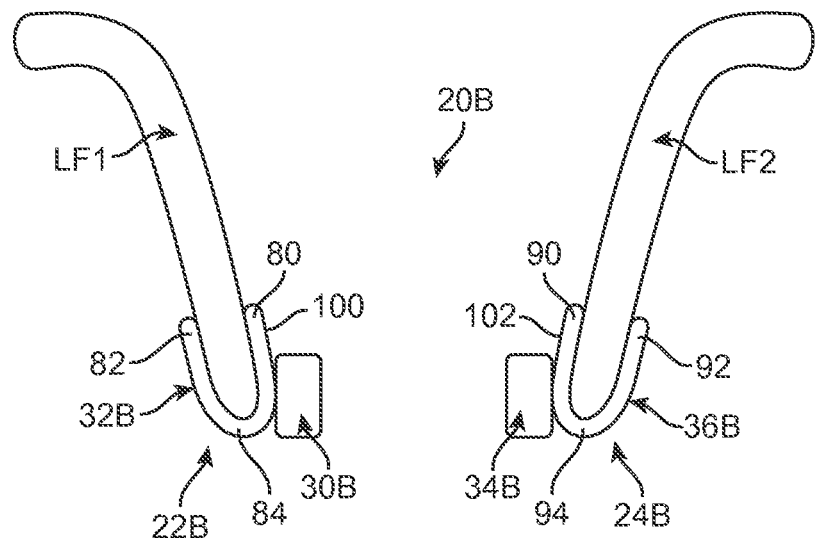
FIG. 4A is a simplified side view of another tissue approximation system in accordance with principles of the present disclosure and as initially applied to two tissue segments.

Another embodiment tissue approximation system 20B in accordance with principles of the present disclosure is shown in FIG. 4A and includes first and second approximation devices 22B, 24B. The first approximation device 22B includes at least one magnetic component 30B and an attachment mechanism 32B. The second approximation device 24B similarly includes at least one magnetic component 34B and an attachment mechanism 36B. The magnetic components 30B, 34B may or may not be identical, and can assume any of the forms described herein. With the embodiment of FIG. 4A, the attachment mechanisms 32B, 36B are highly similar, optionally identical, and include or comprise a clamping structure akin to the embodiment of FIG. 3A. For example, the attachment mechanism 32B of the first approximation device 22B includes opposing side walls 80, 82 and a bottom wall 84. The opposing jaws 80, 82 extend from opposite sides of the bottom wall 84 and can optionally form a toothed or roughened surface. The attachment mechanism 32B is configured such that the opposing side walls 80, 82 can pivot or move relative to one another, for example by configuring the bottom wall 84 to be deformable and optionally configured to self-retain an imparted shape. The bottom wall 84 can deform in allowing the opposing side walls 80, 82 to be forced toward or away from one another. For example, the opposing side walls 80, 82 can be forced apart to generate an enlarged gap there between sufficiently sized for insertion over the tissue segment LF1, and then forced toward one another and held in this closed arrangement by the bottom wall 84 so as to achieve a clamped or crimped fixation to the tissue segment LF1. The attachment mechanism 36B of the second approximation device 24B can similarly include opposing side walls 90, 92 and a deformable bottom wall 94.

Figure 4B:
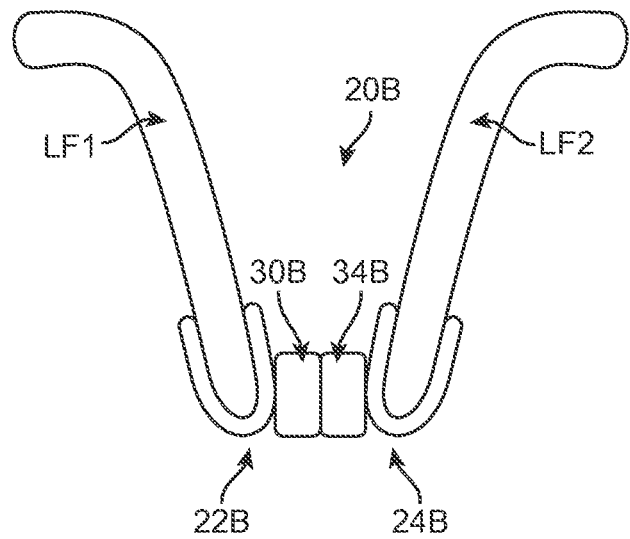
FIG. 4B is a simplified side view of the system of FIG. 4A having directed the tissue segments to an approximated state.

The magnetic component 30B, 34B is mounted or carried by the corresponding attachment mechanism 32B, 36B in a manner promoting a desired spatial arrangement upon connection to the respective tissue segment LF1, LF2. For example, a shape and operation of the attachment mechanism 32B naturally establishes an interior face 100 along the side wall 80 at the intended target site (e.g., with the exemplary embodiment in which the first approximation device 22B is fastened to the first mitral valve leaflet LF1, the interior face 100 naturally faces the second leaflet LF2). The magnetic component 30B can be carried by the side wall 80 at the interior face 100. The magnetic component 34B of the second approximation device 24B is similarly carried at an interior face 102 of the side wall 90. Thus, once applied at the intended target site, the magnetic components 30B, 34B are arranged to "face" one another; in related embodiments in which the magnetic components 30B, 34B each include one or more magnetized elements, the spatial arrangement established by the approximation devices 22B, 24B upon coupling to the respective tissue segments LF1, LF2 (in an expected manner) provides the complementary magnetic pole arrangement as described above. Regardless, upon connection to the respective tissue segments LF1, LF2, the approximation devices 22B, 24B transition to the approximated state of FIG. 4B due to the magnetic force(s) described above, and maintain a position of the so-approximated tissue segments LF1, LF2.

Figure 5A:
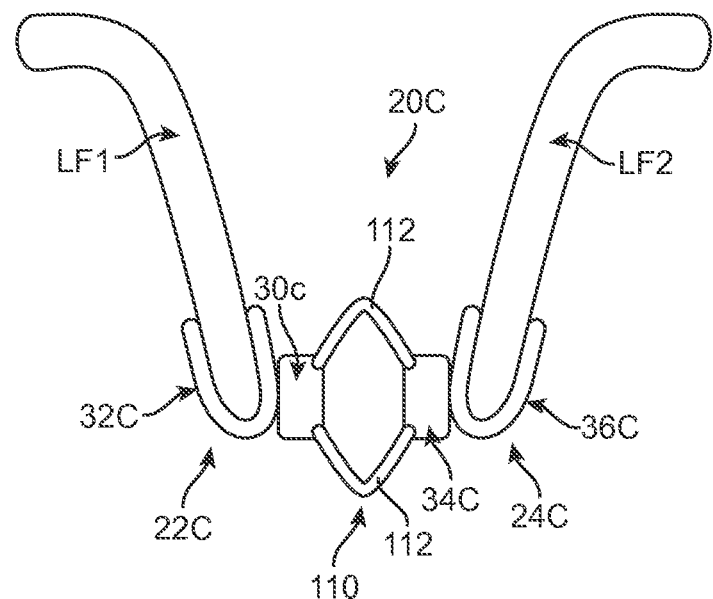
FIG. 5A is a simplified side view of another tissue approximation system in accordance with principles of the present disclosure.
Figure 5B:
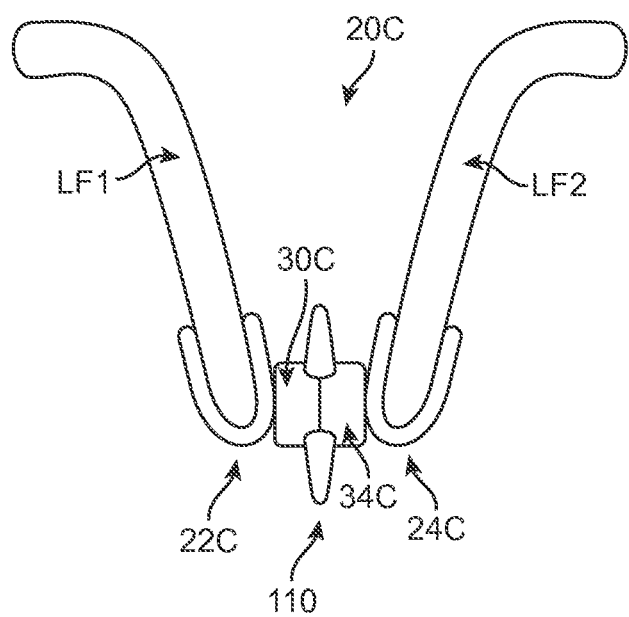
FIG. 5B is a simplified side view of the system of FIG. 5A having directed the tissue segments to an approximated state.

Another embodiment tissue approximation system 20C in accordance with principles of the present disclosure is shown in FIG. 5A and includes first and second approximation devices 22C, 24C and a connection device 110. The first and second approximation devices 22C, 24C can be identical to the approximation devices 22B, 24B (FIG. 4A) as described above, each including a magnetic component 30C, 34C and an attachment mechanism 32C, 36C, respectively. The connection device 110 can assume a variety of forms, and extends between/flexibly connects the approximation devices 22C, 24C. For example, connection device 110 can include one or more tethers 112 (e.g., sutures, wires, strings, etc.) that are attached at opposite ends thereof to the approximation devices 22C, 24C (e.g., at the corresponding magnetic component 30C, 34C). The connection device 110 is sufficiently flexible and is arranged so as to not overtly interfere with the intended magnetic coupling effectuated by the magnetic components 30C, 34C, as reflected by FIG. 5B. That is to say, with the system 20C, the tissue segments LF1, LF2 are approximated and maintained in the so-approximated arrangement. In the event that the target site is subjected to unexpected forces sufficient to overcome the magnetic force/attraction between the magnetic components 30C, 34C and cause the tissue segments LF1, LF2 to separate from one another, the connection device 110 will prevent the tissue segments LF1, LF2 from becoming displaced by too great a distance (i.e., a spacing beyond the magnetic field(s) such that the magnetic components 30C, 34C are no longer magnetically drawn toward one another). Once the anatomical force or condition giving rise to the forced separation subsides, the magnetic components 30C, 34C are sufficiently close to one another for the magnetic field(s) to return the system 20C (and thus the tissue segments LF1, LF2) to the approximated state of FIG. 5B. The connection device 110 can be incorporated into any of the approximation systems of the present disclosure.

Figure 6A:
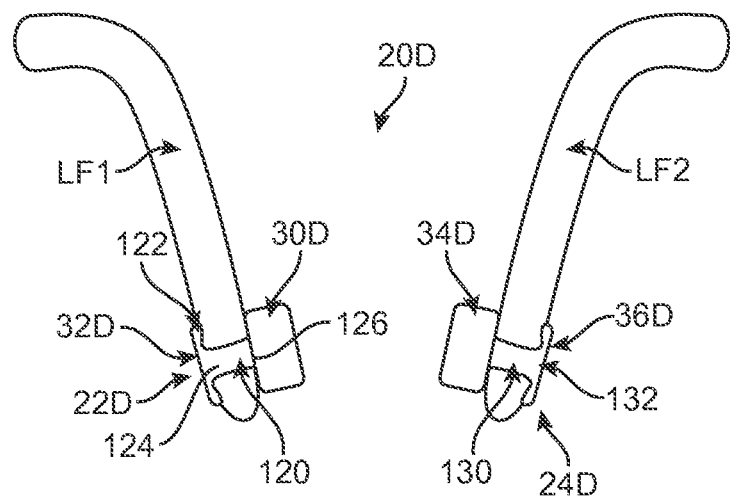
FIG. 6A is a simplified side view of another tissue approximation system in accordance with principles of the present disclosure and as initially applied to two tissue segments.

Another embodiment tissue approximation system 20D in accordance with principles of the present disclosure is shown in FIG. 6A and includes first and second approximation devices 22D, 24D. The first approximation device 22D includes at least one magnetic component 30D and an attachment mechanism 32D. The second approximation device 24D similarly includes at least one magnetic component 34D and an attachment mechanism 36D. The magnetic components 30D, 34D may or may not be identical, and can assume any of the forms described herein. With the embodiment of FIG. 6A, the attachment mechanisms 32D, 36D are highly similar, optionally identical, and are configured for rivet-like fastening to the respective tissue segment LF1, LF2. For example, the attachment mechanism 32D of the first approximation device 22D includes a post 120 and a base 122. A length of the post 120 is selected in accordance with an expected thickness of the target tissue segment LF1 (e.g., a length of the post 120 approximates or is slightly greater or lesser than an expected thickness of the target tissue segment LF1). The post 120 is configured for insertion through a thickness of the target tissue segment LF1 and has a diameter less than a width (or outer major dimension) of the base 122 and the magnetic component 30D. Upon final assembly to the tissue segment LF1, then, the magnetic component 30D and the base 122 are held at opposite sides of the tissue segment LF1 by the post 120.

The post 120 can be viewed as having or defining opposing, first and second ends 124, 126. The first end 124 is associated with the base 122 and the second end 126 is associated with the magnetic component 30D. With this in mind, the post 120 is configured to be releasably secured to one or both of the base 122 or the magnetic component 30D. For example, in some embodiments, the first end 124 is permanently attached to the base 122, whereas the second end 126 is selectively secured to the magnetic component 30D. For example, the magnetic component 30D can form an opening and/or incorporate other structural features or mechanisms configured to frictionally and/or mechanically receive the second end 126. Alternatively or in addition, with embodiments in which the magnetic component 30D includes a magnetized element, the post 120, or at least the second end 126, can be formed of a material configured to be magnetically attracted to the corresponding side of the magnetic component 30D (or vice-versa). Regardless, with this one optional construction, the attachment mechanism 34D is connected to the corresponding tissue segment LF1 by inserting the second end 126 through a thickness of the tissue segment LF1 (e.g., via a pre-made hole and/or by piercing the second end 126 through the tissue segment LF1) until the second end 126 is accessible at a side of the tissue segment LF1 opposite the base 122; the magnetic component 30D can then be assembled to the so-exposed second end 126.

Alternatively, the second end 126 can be permanently coupled to the magnetic component 30D, whereas the first end 124 is selectively secured to the base 122 in accordance with any of the descriptions herein. With these alternative constructions, the magnetic component 30D and the attachment mechanism 34D are installed to the tissue segment LF1 by inserting the first end 124 through a thickness of the tissue segment LF1 (e.g., pre-formed hole and/or by piercing the first end through the tissue segment LF1) until the first end 124 is accessible at a side of the tissue segment LF1 opposite the magnetic component 30D; the base 122 is then assembled to the so-exposed first end 124.

The second approximation device 24D can have any of the configurations described above with respect to the first approximation device 22D. Thus, for example, the attachment mechanism 36D can have a post 130 and a base 132.

Figure 6B:
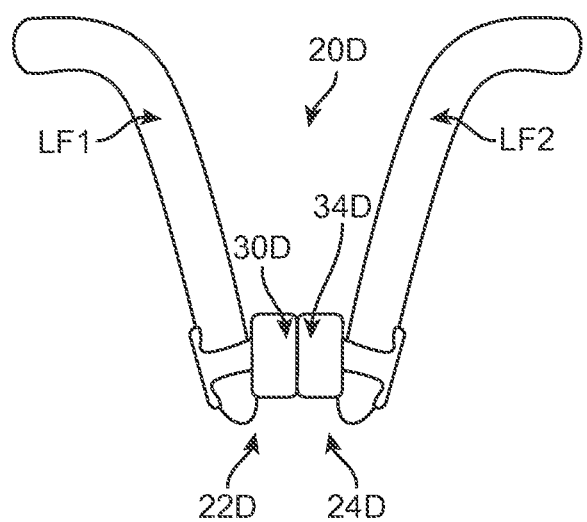
FIG. 6B is a simplified side view of the system of FIG. 6A having directed the tissue segments to an approximated state.

The magnetic component 30D, 34D is mounted or carried by the corresponding attachment mechanism 32D, 36D in a manner promoting a desired spatial arrangement upon connection to the respective tissue segment LF1, LF2. Thus, once applied at the intended target site, the magnetic components 30D, 34D are arranged to "face" one another; in related embodiments in which the magnetic components 30D, 34D each include one or more magnetized elements, the spatial arrangement established by the approximation devices 22D, 24D upon coupling to the respective tissue segments LF1, LF2 (in an expected manner) provides the complementary magnetic pole arrangement as described above. Regardless, upon connection to the respective tissue segments LF1, LF2, the approximation devices 22D, 24D transition to the approximated state of FIG. 6B due to the magnetic force(s) described above, and maintain a position of the so-approximated tissue segments LF1, LF2.

Figure 7A:
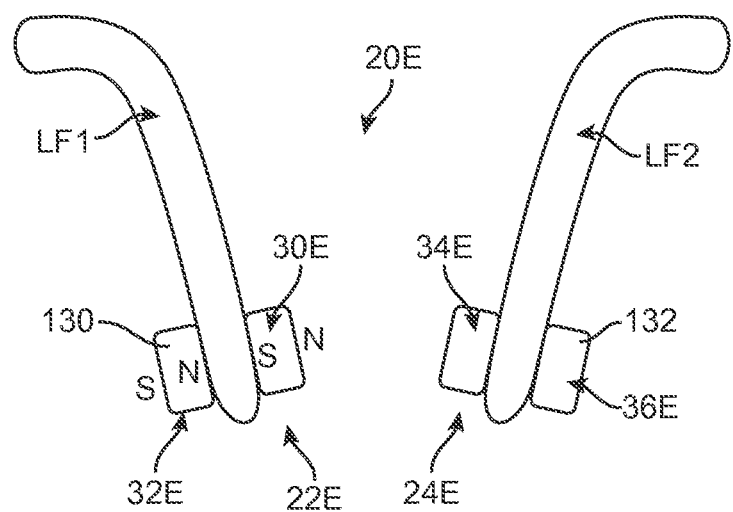
FIG. 7A is a simplified side view of another tissue approximation system in accordance with principles of the present disclosure and as initially applied to two tissue segments.

Another embodiment tissue approximation system 20E in accordance with principles of the present disclosure is shown in FIG. 7A and includes first and second approximation devices 22E, 24E. The first approximation device 22E includes at least one magnetic component 30E and an attachment mechanism 32E. The second approximation device 24E similarly includes at least one magnetic component 34E and an attachment mechanism 36E. The magnetic components 30E, 34E may or may not be identical, and can assume any of the forms described herein. With the embodiment of FIG. 7A, the attachment mechanisms 32E, 36E are highly similar, optionally identical, and are configured for fastening the corresponding magnetic components 30E, 34E to the respective tissue segment LF1, LF2 via a magnetic interface. For example, the attachment mechanism 32E of the first approximation device 22E includes a magnetic body 130. The magnetic body 130 can assume any of the forms described above with respect to the magnetic component 30 (FIG. 2A). In some embodiments, the magnetic body 130 includes a magnetized element; in other embodiments, the magnetic body 130 includes a non-magnetized element that is magnetically attracted to a magnetized element of the magnetic component 30E. Regardless, the magnetic body 130 is configured to magnetically attract and/or be magnetically attracted to the corresponding magnetic component 30E. For example, in some embodiments the magnetic component 30E includes a magnetized element establishing opposing, magnetic poles (represented in FIG. 7A by the letters "N" and "S"); the magnetic body 130 may also include a magnetized element establishing opposing, magnetic poles ("N" and "S"). With these exemplary embodiments, the magnetic component 30E and the attachment mechanism 32E are arranged at opposite sides of the tissue segment LF1 such that opposing poles face one another (e.g., the pole "S" of the magnetic component 30E faces the opposite magnetic pole "N" of the magnetic body 130), thus magnetically attracting the magnetic component 30E and the attachment mechanism 32E toward one another and in turn pinching the tissue segment LF1 between the magnetic component 30E and the attachment mechanism 32E. Upon final assembly to the tissue segment LF1, then, the magnetic component 30E and the attachment mechanism 32E are held at opposite sides of the tissue segment LF1 by a magnetic force.

The second approximation device 24E can have any of the configurations described above with respect to the first approximation device 22E. Thus, for example, the attachment mechanism 36E of the second approximation device 24E can include a magnetic body 132 arranged relative to the tissue segment LF2 so as to magnetically attract and/or be magnetically attracted to the corresponding magnetic component 34E.

Figure 7B:
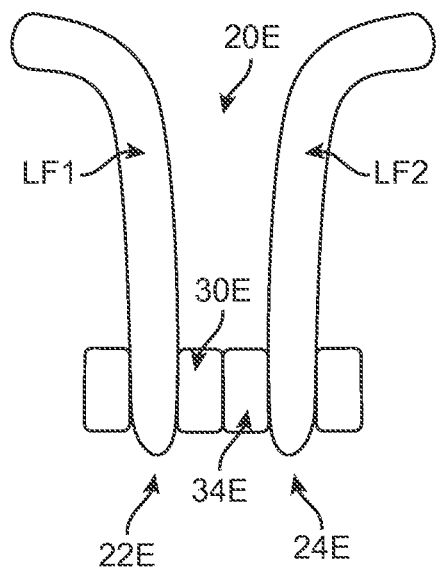
FIG. 7B is a simplified side view of the system of FIG. 7A having directed the tissue segments to an approximated state.

Regardless of an exact construction, the approximation devices 22E, 24E are configured such that once applied at the intended target site, the magnetic components 30E, 34E are arranged to "face" one another; in related embodiments in which the magnetic components 30E, 34E each include one or more magnetized elements, the spatial arrangement established by the approximation devices 22E, 24E upon coupling to the respective tissue segments LF1, LF2 (in an expected manner) provides the complementary magnetic pole arrangement as described above. Upon connection to the respective tissue segments LF1, LF2, the approximation devices 22E, 24E transition to the approximated state of FIG. 7B due to the magnetic force(s) described above, and maintain a position of the so-approximated tissue segments LF1, LF2.

Figure 8A:
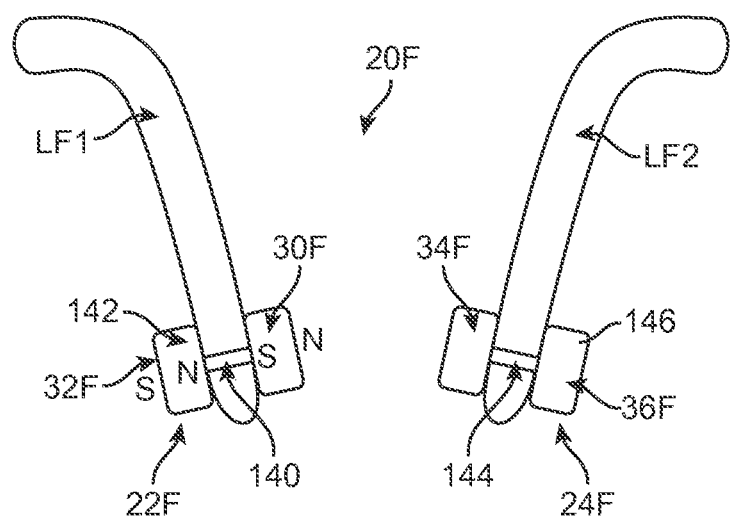
FIG. 8A is a simplified side view of another tissue approximation system in accordance with principles of the present disclosure and as initially applied to two tissue segments.

Another embodiment tissue approximation system 20F in accordance with principles of the present disclosure is shown in FIG. 8A and includes first and second approximation devices 22F, 24F. The first approximation device 22F includes at least one magnetic component 30F and an attachment mechanism 32F. The second approximation device 24F similarly includes at least one magnetic component 34F and an attachment mechanism 36F. The magnetic components 30F, 34F may or may not be identical, and can assume any of the forms described herein. With the embodiment of FIG. 8A, the attachment mechanisms 32F, 36F are highly similar, optionally identical, and are configured for fastening the corresponding magnetic component 30F, 34F to the respective tissue segment LF1, LF2 via mechanical and magnetic interfaces. The attachment mechanisms 32F, 36F can include or incorporate features described above with respect to the system 20D of FIG. 6A and the system 20E of FIG. 7A.

For example, the attachment mechanism 32F of the first approximation device 22F includes a post 140 and a magnetic base 142. A length of the post 140 is selected in accordance with an expected thickness of the target tissue segment LF1 (e.g., a length of the post 140 approximates or is slightly greater or lesser than an expected thickness of the target tissue segment LF1). The post 140 is configured for insertion through a thickness of the target tissue segment LF1 and has a diameter less than a width (or outer major dimension) of the magnetic base 142 and the magnetic component 30F. Upon final assembly to the tissue segment LF1, then, the magnetic component 30F and the magnetic base 142 are supported relative to opposite sides of the tissue segment LF1 by the post 140. As with the attachment mechanism 32D (FIG. 6A) described above, the approximation device 22F can be configured such that the post 140 is selectively secured to one of the magnetic component 30F or the magnetic base 142, and is permanently secured to the other of the magnetic component 30F or the magnetic base 142.

The magnetic base 142 can assume any of the forms described above with respect to the magnetic component 30 (FIG. 2A). In some embodiments, the magnetic base 142 includes a magnetized element; in other embodiments, the magnetic base 142 includes a non-magnetized element that is magnetically attracted to a magnetized element of the magnetic component 30F. Regardless, the magnetic base 142 is configured to magnetically attract and/or be magnetically attracted to the corresponding magnetic component 30F. For example, in some embodiments the magnetic component 30F includes a magnetized element establishing opposing, magnetic poles (represented in FIG. 8A by the letters "N" and "S"); the magnetic base 142 may also include a magnetized element establishing opposing, magnetic poles ("N" and "S"). With these exemplary embodiments, the magnetic component 30F and the attachment mechanism 32F are arranged at opposite sides of the tissue segment LF1 such that opposing poles face one another (e.g., the pole "S" of the magnetic component 30F faces the opposite magnetic pole "N" of the magnetic base 142), thus magnetically attracting the magnetic component 30F and the attachment mechanism 32F toward one another and in turn pinching the tissue segment LF1 between the magnetic component 30F and the magnetic base 142. Upon final assembly to the tissue segment LF1, then, the magnetic component 30E and the magnetic base 142 are held at opposite sides of the tissue segment LF1 by a magnetic force.

The second approximation device 24F can have any of the configurations described above with respect to the first approximation device 22F. Thus, for example, the attachment mechanism 36F of the second approximation device 24F can include a post 144 interconnecting the magnetic component 34F with a magnetic base 146 otherwise arranged relative to the tissue segment LF2 so as to magnetically attract and/or be magnetically attracted to the corresponding magnetic component 34F.

Figure 8B:
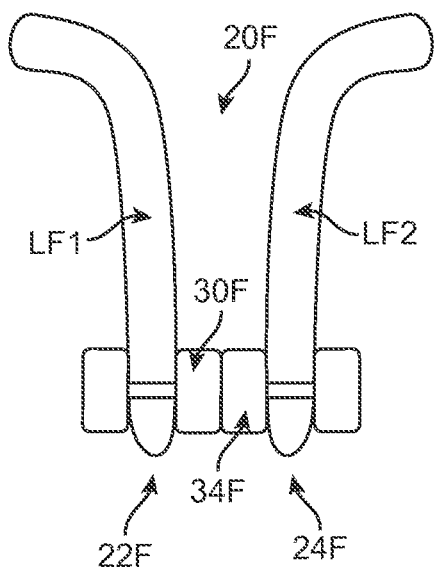
FIG. 8B is a simplified side view of the system of FIG. 8A having directed the tissue segments to an approximated state.

Regardless of an exact construction, the approximation devices 22F, 24F are configured such that once applied at the intended target site, the magnetic components 30F, 34F are arranged to "face" one another; in related embodiments in which the magnetic components 30F, 34F each include one or more magnetized elements, the spatial arrangement established by the approximation devices 22F, 24F upon coupling to the respective tissue segments LF1, LF2 (in an expected manner) provides the complementary magnetic pole arrangement as described above. Upon connection to the respective tissue segments LF1, LF2, the approximation devices 22F, 24F transition to the approximated state of FIG. 8B due to the magnetic force(s) described above, and maintain a position of the so-approximated tissue segments LF1, LF2.

Figure 9A:
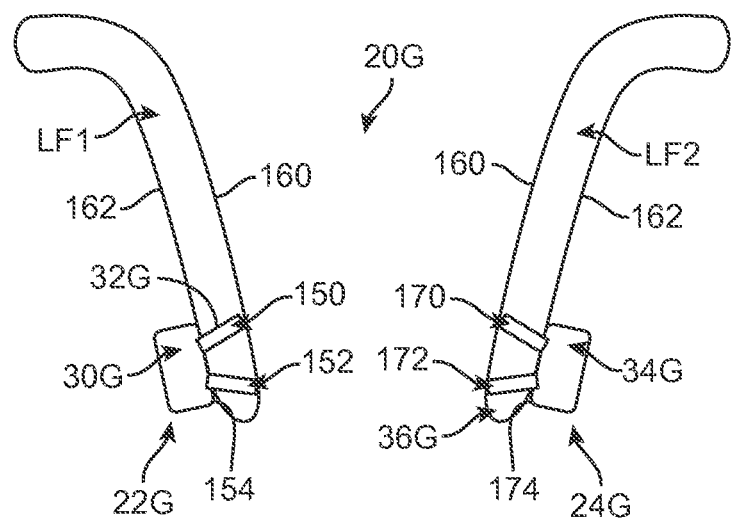
FIG. 9A is a simplified side view of another tissue approximation system in accordance with principles of the present disclosure and as initially applied to two tissue segments.

Another embodiment tissue approximation system 20G in accordance with principles of the present disclosure is shown in FIG. 9A and includes first and second approximation devices 22G, 24G. The first approximation device 22G includes at least one magnetic component 30G and an attachment mechanism 32G. The second approximation device 24G similarly includes at least one magnetic component 34G and an attachment mechanism 36G. The magnetic components 30G, 34G may or may not be identical, and can assume any of the forms described herein. With the embodiment of FIG. 9A, the attachment mechanisms 32G, 36G are highly similar, optionally identical, and are configured to embed within a thickness of the corresponding tissue segment LF1, LF2. For example, the attachment mechanism 32G of the first approximation device 22G includes at least first and second pins 150, 152. The pins 150, 152 are attached to and rigidly extend from an interior face 154 of the magnetic component 30G, and are configured to pierce through tissue of the tissue segment LF1. The pins 150, 152 can project in a non-perpendicular fashion relative to one another so as to more robustly engage the tissue segment LF1 during insertion. As a point of reference, each of the tissue segments LF1, LF2 can be viewed as defining an interior side 160 and an exterior side 162. In some embodiments, the approximation device 22G is configured to promote an installation methodology whereby the approximation device 22G is initially arranged slightly outside of the exterior side 160 and then forced or pressed toward the tissue segment LF1. With this approach, the pins 150, 152 pierce through the exterior side 162 and then progress toward the interior side 160. Once fully inserted, the magnetic component 30G is arranged at or against the exterior side 162 (as compared to other embodiments in which the magnetic components are arranged at or against the interior side of the corresponding tissue segment).

The second approximation device 24G can have any of the configurations described above with respect to the first approximation device 22G. Thus, for example, the attachment mechanism 36G of the second approximation device 24G can include opposing pins 170, 172 projecting from an interior face 174 of the corresponding magnetic component 34G and otherwise arranged such that upon final implantation, the magnetic components 34G can be held at or against the exterior side 162 of the tissue segment LF2.

Figure 9B:
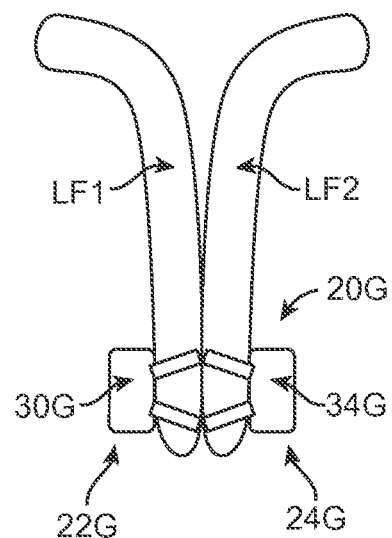
FIG. 9B is a simplified side view of the system of FIG. 9A having directed the tissue segments to an approximated state.

Regardless of an exact construction, the approximation devices 22G, 24G are configured such that once applied at the intended target site, the magnetic components 30G, 34G are arranged to "face" one another albeit at the exterior side 162 of the corresponding tissue segment LF1, LF2; in related embodiments in which the magnetic components 30G, 34G each include one or more magnetized elements, the spatial arrangement established by the approximation devices 22G, 24G upon coupling to the respective tissue segments LF1, LF2 (in an expected manner) provides the complementary magnetic pole arrangement as described above. Upon connection to the respective tissue segments LF1, LF2, the approximation devices 22G, 24G transition to the approximated state of FIG. 9B due to the magnetic force(s) described above, and maintain a position of the so-approximated tissue segments LF1, LF2.

Figure 10:
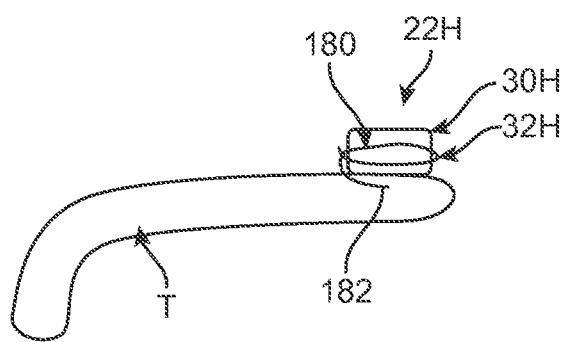
FIG. 10 is a simplified side view of a portion of another embodiment tissue approximation system in accordance with principles of the present disclosure as applied to a tissue segment.

The tissue approximation systems of the present disclosure are in no way limited to the attachment mechanism configurations described herein. A number of other devices, mechanisms and/or techniques are equally acceptable for associating a magnet component with a tissue segment. For example, FIG. 10 illustrates an approximation device 22H useful with any of the systems described herein relative to a tissue segment T. The approximation device 22H includes a magnetic component 30H and an attachment mechanism 32H. The magnetic component 30H can assume any of the forms described above. The attachment mechanism 32H includes a wire 180 that is wound about or otherwise secured to the magnetic component 30H and provides a leading end 182 configured to pierce into the tissue segment T. The wire 180 can have various forms, and in some embodiments is formed of a shape memory material, such as a nickel titanium alloy (NiTi™) as is known in the art. Regardless, the approximation device 22H can be assembled to the tissue segment T by forcing the leading end 182 an appreciable distance into a thickness of the tissue segment T (e.g., piercing the tissue segment T with the leading end and then rotating the approximation device 22H to further progress the wire 180 into the tissue segment T).

Figure 11:
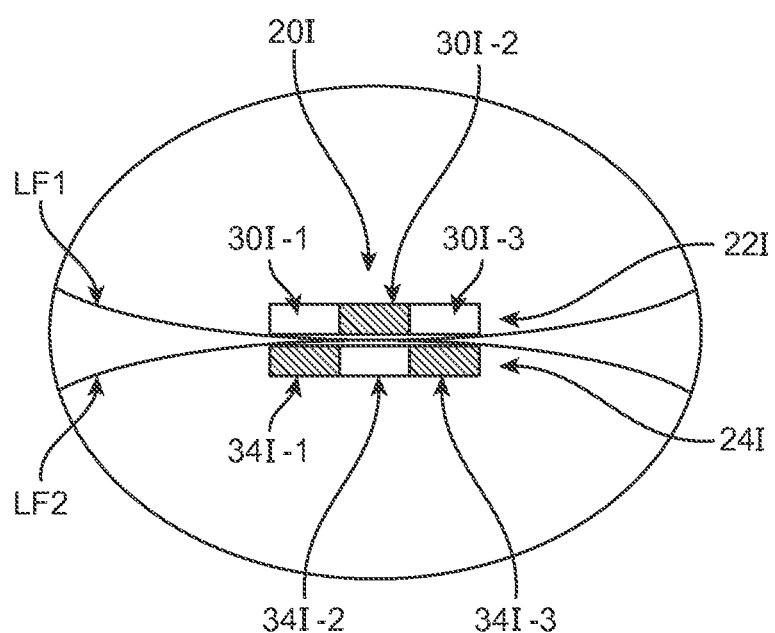
FIG. 11 is a simplified top view of another embodiment tissue approximation system in accordance with principles of the present disclosure as applied to two tissue segments.

In yet other embodiments, the magnetic component(s) can be configured for self-connection or attachment to the corresponding tissue segment. For example, another embodiment tissue approximation system 20I in accordance with principles of the present disclosure is shown in simplified form in FIG. 11 as applied to tissue segments LF1, LF2. The system 20I includes first and second approximation devices 22I, 24I that can, in some embodiments, be highly similar. The first approximation device 22I includes a plurality of magnetic components 30I-1, 30I-2, 30I-3 that can take any of the forms described above; the second approximation device 24I similarly includes a plurality of magnetic components 34I-1, 34I-2, 34I-3 that can also assume any of the forms described above. As reflected by shading in FIG. 11, the magnetic components 30I, 34I are arranged relative to the corresponding tissue segment LF1, LF2 as magnetic pairs (e.g., the magnetic components 30I-1, 34I-1 are arranged opposite one another and have opposing magnetic poles facing each other). While FIG. 11 reflects the system 20I as having three magnetic pairs, any other number, either greater or lesser, is equally acceptable. Upon deployment to the target site, the magnetic forces of the magnetic pairs approximate the tissue segments LF1, LF2 and serve to retain the magnetic components 30I, 34I against the corresponding tissue segment LF1, LF2. Further, with the system 20I of FIG. 11 (as well as other systems of the present disclosure), a user is afforded the ability to tailor the system 20I to achieve a desired amount or level of tissue approximation (e.g., leaflet apposition). For example, if it is determined, after installing a first pair of the magnetic components 30I-1, 34I-1 to the opposing mitral valve leaflets, that regurgitation continued to occur, additional pair(s) of the magnetic components 30I, 34I could be added.

Figure 12:
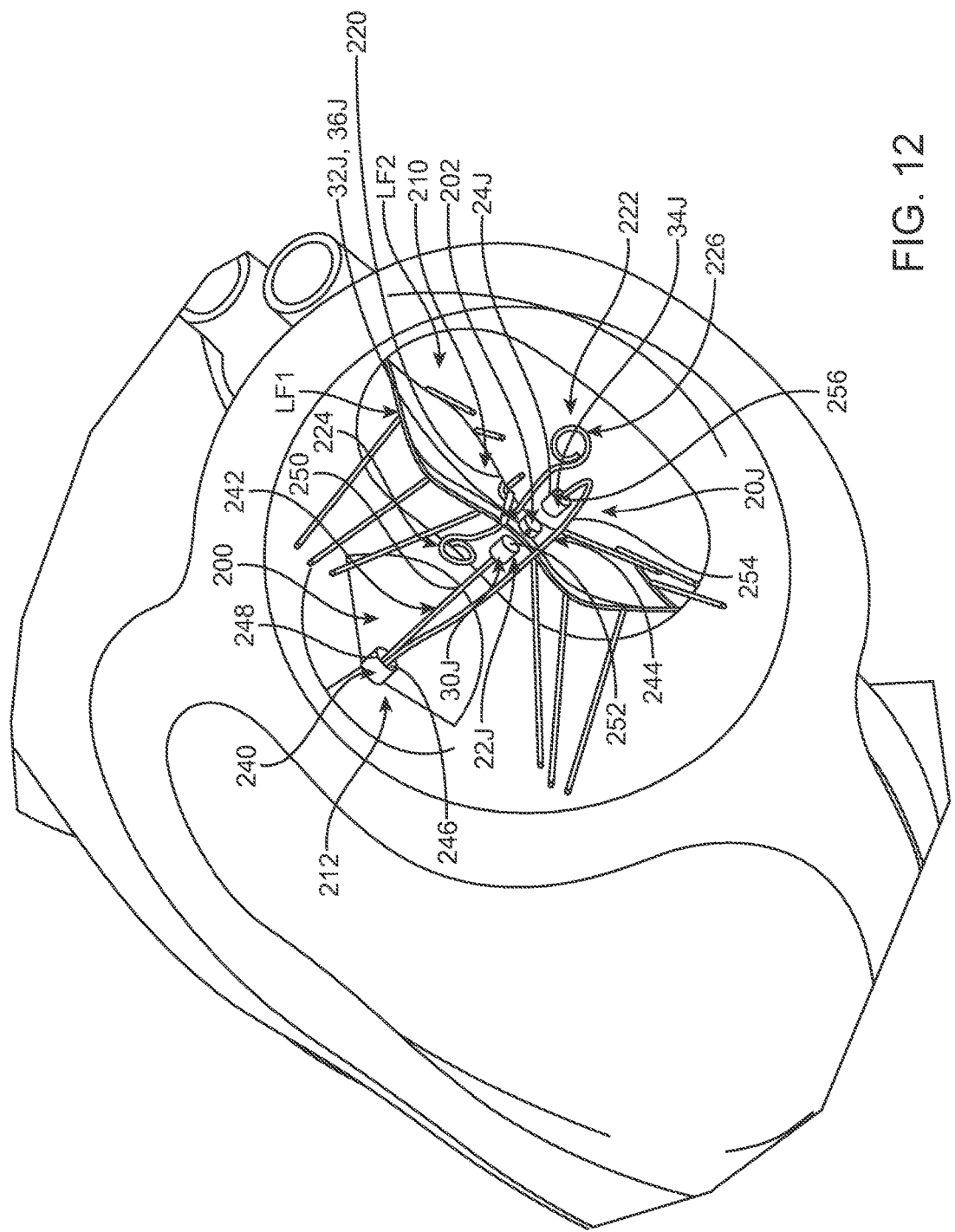
FIG. 12 is a partial cross-sectional view of the human heart from a perspective of the apex of the heart and illustrates portions of a tissue approximation system and of a delivery system in accordance with principles of the present disclosure.

Regardless of exact form, the approximation devices of the present disclosure can be delivered to the target site in various manners using a variety of delivery tools, optionally on a minimally invasive basis. For example, FIG. 12 illustrates (from a perspective of the apex of the human heart) another embodiment tissue approximation system 20J in accordance with principles of the present disclosure being deployed to the opposing leaflets LF1, LF2 of a mitral valve target site via a delivery system 200 (referenced generally). The approximation system 20J includes a first tissue approximation device 22J and a second tissue approximation device 24J. The approximation devices 22J, 24J each include a magnetic component 30J, 34J, respectively, that can have any of the forms described above. In addition, the devices 22J, 24J each include an attachment mechanism 32J, 36J that, with the one embodiment of FIG. 12, are commonly defined or generated by a magnetic body 202. A magnetic attribute of the magnetic body 202 is such that the magnetic body 202 magnetically attracts and/or is magnetically attracted to, a magnetic pole established at an interior face of both of the magnetic components 30J, 34J. In other words, in the arrangement of FIG. 12, both of the magnetic components 30J, 34J are magnetically attracted to and/or magnetically attract the magnetic body 202 such that upon release from corresponding tools of the delivery system 200, the magnetic components 30J, 34J will approximate the tissue segments LF1, LF2 on to the magnetic body 202. The delivery system 200 can alternatively be useful with any other tissue approximation systems of the present disclosure and is not limited to the particular configuration of FIG. 12 (i.e., in other embodiments, the delivery system 200 can be used to deliver tissue approximation devices that may or may not include the magnetic body that otherwise provides a common attachment mechanism).

The delivery system 200 can incorporate various features appropriate for achieving the spatial arrangements of the exemplary mitral valve procedure of FIG. 12 on a minimally invasive basis. For example, in some embodiments, the delivery system 200 includes a first delivery tool 210 (referenced generally) and a second delivery tool 212. The delivery tools 210, 212 are separately provided, and can be manipulated independent of one another in accessing the target site from opposite sides.

The first delivery tool 210 is generally configured for delivering the magnetic body 202 to the target site as well as for capturing the leaflets LF1, LF2 via a transeptal or transatrial (or similar) approach to the mitral valve target site. The first delivery tool 210 can include a delivery catheter (not shown) slidably maintaining a shaft 220 (primarily hidden in the view) and a capture device 222. The shaft 220 can be a wire or similar structure, and is configured to selectively retain the magnetic body 202. The capture device 222 can assume various forms for capturing the leaflets LF1, LF2 when deployed from the delivery catheter. For example, the capture device 222 can include first and second arms 224, 226 as shown. The arms 224, 226 can be wire-like bodies each configured to self-revert to (e.g., shape memory material), or be directed to (e.g., via at least one pull wire or similar mechanisms), a predetermined shape when exposed distal the delivery catheter appropriate for capturing a respective one of the leaflets LF1, LF2. With the exemplary embodiment of FIG. 12, the arms 224, 226 are shaped to project outwardly and proximally in the deployed state shown, with the first arm 224 extending opposite the second arm 226. Other leaflet-capturing designs are equally acceptable. The arms 224, 226 readily collapse when located within the delivery catheter for low profile, transcatheter delivery (or other minimally invasive technique) to the target site.

The second delivery tool 212 is generally configured for delivering the magnetic components 30J, 34J to the mitral valve target site via a transaortic or transapical approach, and can include a catheter 240, a first shaft 242 and a second shaft 244. The catheter 240 can assume any form known in the art, generally configured to be guided through a patient's vasculature to the aortic valve and left ventricle as shown. The catheter 240 forms a lumen 246 within which the shafts 242, 244 are slidably received. The lumen 246 is open at a distal end 248 of the catheter 240. The shafts 242, 244 can be solid or hollow bodies, and in some embodiments each includes one or more wires formed of a shape memory material. The first shaft 242 includes a distal section 250 terminating at a shaft end 252. The shaft end 252 is configured to selectively maintain the magnetic component 30J (e.g., frictional fit, one more retention mechanism, etc.), with at least the distal section 250 configured to self-revert to a shape appropriate for locating the shaft end 252 (and thus the magnetic component 30J) adjacent the first leaflet LF1 when exposed distally beyond the catheter distal end 248. The second shaft 244 similarly includes a distal section 254 terminating at a shaft end 256 configured to selectively maintain the magnetic component 34J. The distal section 254 of the second shaft 244 is configured to self-revert to the curved shape shown when exposed distal the catheter distal end 248, thus presenting the magnetic component 34J adjacent the second leaflet LF2. The distal sections 250, 254 readily collapse when located within the catheter 240 for low profile, transcatheter delivery (or other minimally invasive technique) to the target site. The second delivery tool 212 can assume a wide variety of other forms, and can include structures or mechanisms not directly implicated by FIG. 12.

During use, the first delivery tool 210 is percutaneously delivered to the mitral valve target site via the patient's vasculature, with the shaft 220 (and thus the magnetic body 202 carried thereby) and the capture device 222 constrained within the delivery catheter (not shown). For example, the delivery catheter can be routed through the femoral vein, into the right atrium, and then across the septum through a punctured hole by following a guide wire, through an introducer, or by direct navigation. The delivery catheter distal end is thus directed into left atrium and positioned immediately proximate the mitral valve (e.g., at the inflow side of the mitral valve). The capture device 222 is then deployed from the delivery catheter, with the arm 224, 226 being directed to or toward the pre-determined shapes and spatial orientations as shown. In the deployed state, the first arm 224 engages or captures the first leaflet LF1 and the second arm 226 engages or captures the second leaflet LF2 (e.g., the arms 224, 226 can initially be deployed in the left ventricle at a location beyond the leaflets LF1, LF2 and then proximally retracted to capture the corresponding leaflet LF1, LF2). Prior to, after, or simultaneously with capturing of the leaflets LF1, LF2, the shaft 220 is deployed from the delivery catheter, locating the magnetic body 202 between the leaflets LF1, LF2.

The second delivery tool 212 is also percutaneously delivered to the mitral valve target site via the patient's vasculature, with the shafts 242, 244 (and thus the magnetic components 30J, 34J carried thereby) retracted within the catheter 240. For example, in one non-limiting embodiment, the catheter 240 is directed through the vasculature to the aortic arch and then to the aorta. The distal end 248 is located beyond or adjacent the aortic valve, optionally within the left ventricle. Regardless, the shafts 242, 244 (including the magnetic components 30J, 34J carried thereby) are then deployed from the catheter 240, locating the magnetic components 30J, 34J in close proximity to the corresponding, captured leaflet LF1, LF2.

Once the delivery tools 210, 212 are arranged as shown in FIG. 12, the magnetic components 30J, 34J are magnetically attracted to and/or magnetically attract the magnetic body 202, as well as optionally being magnetically attracted to each other. Due to this magnetic attraction, the first leaflet LF1 becomes pinched or captured between the magnetic component 30J and the magnetic body 202; the second leaflet LF2 similarly becomes pinched or captured between the magnetic component 34J and the magnetic body 202. As a result, the leaflets LF1, LF2 are approximated, separated by a thickness of the magnetic body 202, and maintained in the approximated state by the magnetic forces by and between the magnetic components 30J, 34J and the magnetic component 202. The magnetic body 202 can then be released from the shaft 220, and the capture device 222 can be retracted back into the delivery catheter. The first delivery tool 210 can then be removed from the patient. Similarly, the magnetic components 30J, 34J can then be released from the corresponding shaft 242, 244, the shafts 242, 244 retracted into the catheter 240, and the second delivery tool 212 withdrawn. The magnetic components 30J, 34J and the magnetic body 202 remain within the patient, ensuring that the approximated state of the leaflets LF1, LF2 is maintained.

The approximation devices disclosed herein can also be delivered in an open surgical setting via delivery methods that will be understood by one of skill in the art pertaining to tissue approximation, particularly in view of the present disclosure.

Figure 13:
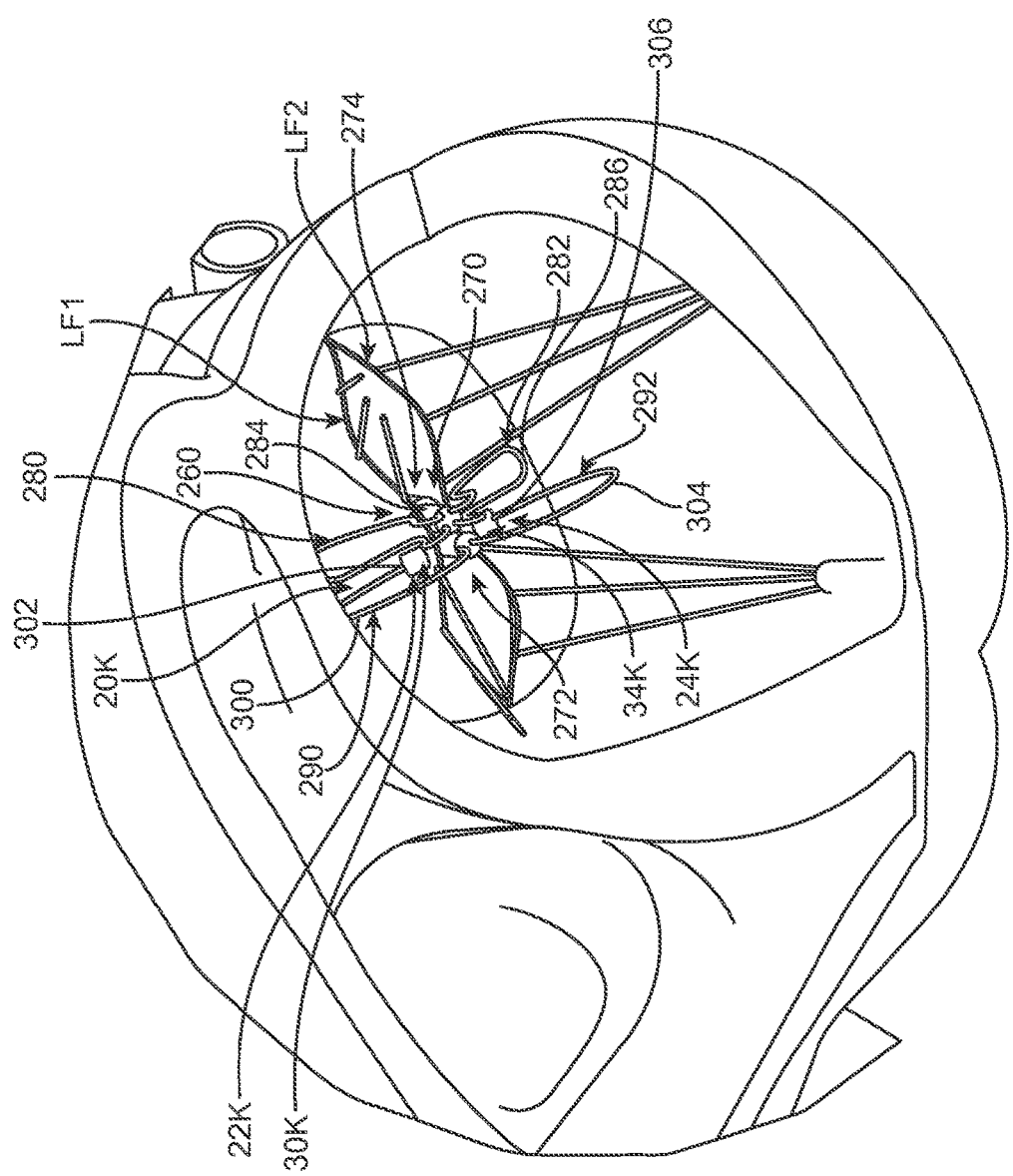
FIG. 13 is a partial cross-sectional view of the human heart from a perspective of the apex of the heart and illustrates portions of another tissue approximation system and if another delivery system in accordance with principles of the present disclosure.

While the present disclosure is in no way limited to approximation of the mitral valve leaflets, with mitral valve applications, the delivery systems of the present disclosure can incorporate other features for capturing the mitral valve leaflets. For example, FIG. 13 illustrates (from a perspective of the apex of the human heart) another embodiment tissue approximation system 20K (referenced generally) in accordance with principles of the present disclosure being deployed to the opposing leaflets LF1, LF2 of a mitral valve target site via a delivery system 260 (referenced generally). The approximation system 20K includes a first tissue approximation device 22K and a second tissue approximation device 24K. The approximation devices 22K, 24K each include a magnetic component 30K, 34K, respectively, that can have any of the forms described herein. In addition, the devices 22K, 24K can each include an attachment mechanism (not shown) that can assume any of the forms described or implicated by the present disclosure (including, but not limited to, the magnetic body 202 (FIG. 12)). Upon release from corresponding tools of the delivery system 260, the magnetic components 30K, 34K will approximate the tissue segments LF1, LF2. The delivery system 260 can alternatively be useful with any other tissue approximation systems of the present disclosure and is not limited to the particular configuration of FIG. 13.

The delivery system 260 can incorporate various features appropriate for achieving the spatial arrangements of the exemplary mitral valve procedure of FIG. 13 on a minimally invasive basis. For example, in some embodiments, the delivery system 260 includes a first delivery tool 270 and a second delivery tool 272. The delivery tools 270, 272 are separately provided but can be commonly carried within a delivery catheter 274. Alternatively, a separate delivery catheter can be provided with each of the delivery tools 270, 272. Regardless, the delivery tools 270, 272 can be manipulated independent of one another in accessing the target site from the same side of the mitral valve.

The first delivery tool 270 is generally configured for capturing the leaflets LF1, LF2 via a transeptal or transatrial (or similar) approach to the mitral valve target site. The first delivery tool 270 includes a capture device having a variety of forms, and in some embodiments comprises opposing, first and second arms 280, 282 and an optional deployment shaft 284. The first and second arms 280, 282 can assume various forms for capturing the leaflets LF1, LF2 when deployed from the delivery catheter. For example, the arms 280, 282 can be wire-like bodies each configured to self-revert to (e.g., shape memory material), or be directed to (e.g., via pull wire(s) or similar mechanisms), a predetermined shape when exposed distal the delivery catheter appropriate for capturing a respective one of the leaflets LF1, LF2. With the exemplary embodiment of FIG. 13, the arms 280, 282 are defined by a continuous wire that is slidably assembled to the deployment shaft 284 and forming a loop end 286. The arms 280, 282 can be retracted into the deployment shaft 284 with only the corresponding loop end 286 being exposed at a distal tip of the shaft 284 thereby establishing a low profile conducive to transcatheter or other minimally invasive delivery. When advanced relative to the distal tip, the wires form to the shape reflected by FIG. 13 to establish the arms 280, 282. The arms 280, 282 are shaped to project outwardly and proximally in the deployed state shown, with the first arm 280 extending opposite the second arm 282. Other leaflet-capturing designs are equally acceptable.

The second delivery tool 272 is generally configured for delivering the magnetic components 30K, 34K to the mitral valve target site via a transeptal or transatrial (or similar) approach, and can include a first shaft 290 and a second shaft 292. The shafts 290, 292 can be solid or hollow bodies, and in some embodiments each includes one or more wires formed of a shape memory material. The first shaft 290 includes a distal section 300 terminating at a shaft end 302. The shaft end 302 is configured to selectively maintain the magnetic component 30K (e.g., frictional fit, one or more retention mechanisms, etc.), with at least the distal section 300 configured to self-revert to a shape appropriate for locating the shaft end 302 (and thus the magnetic component 30K) adjacent the first leaflet LF1 when distally exposed (i.e., the curved shape shown). The second shaft 292 similarly includes a distal section 304 terminating at a shaft end 306 configured to selectively maintain the magnetic component 34K. The distal section 304 of the second shaft 292 is configured to self-revert to the curved shape shown when distally exposed, thus presenting the magnetic component 34K adjacent the second leaflet LF2. The shafts 290, 292 readily collapse when located within the delivery catheter 274 for low profile, transcatheter delivery (or other minimally invasive technique) to the target site. The second delivery tool 272 can assume a wide variety of other forms, and can include structures or mechanisms not directly implicated by FIG. 13. For example, other magnetic component retention mechanisms can include a collapsing hub, a collapsing key, etc.

During use, the first and second delivery tools 270, 272 are percutaneously delivered to the mitral valve target site via the patient's vasculature, with the arms 280, 282 and the shafts 290, 292 maintained within the corresponding delivery catheter. With embodiments including the common delivery catheter 274, the delivery catheter 274 can be routed through the femoral vein, into the right atrium, and then across the septum through a punctured hole by following a guide wire, through an introducer, or by direct navigation. The delivery catheter 274 distal end is thus directed into the left atrium and positioned immediately proximate the mitral valve (e.g., at the inflow side of the mitral valve). The first delivery tool 270 is then deployed from the delivery catheter 274, with the arms 280, 282 being directed to or toward the pre-determined shapes and spatial orientations as shown. In the deployed state, the first arm 280 engages or captures the first leaflet LF1 and the second arm 282 engages or captures the second leaflet LF2 (e.g., the arms 280, 282 can initially be deployed in the left ventricle at a location beyond the leaflets LF1, LF2 and then proximally retracted to capture the corresponding leaflet LF1, LF2).

The second delivery tool 272 is then operated to deploy the magnetic components 30K, 34K. The shafts 290, 292 (including the magnetic components 30K, 34K carried thereby) are deployed from the catheter 274, locating the magnetic components 30K, 34K in close proximity to the corresponding, captured leaflet LF1, LF2. The second delivery tool 272 can further be manipulated to effectuate attachment of the approximation devices 22K, 24K to the corresponding leaflet LF1, LF2 as a function of the attachment mechanism (if any) provided with the device 22K, 24K.

Once the approximation devices 22K, 24K are associated with the corresponding leaflet LF1, LF2 (e.g., directly connected to the leaflet LF1, LF2 by an attachment mechanism, indirectly associated via a centrally placed magnetic body as in FIG. 12, etc.), the magnetic components 30K, 34K can then be released from the corresponding shaft 290, 292, and the second delivery tool 272 withdrawn from the patient. Similarly, the arms 280, 282 can be retracted and the first delivery tool 270 withdrawn. The magnetic components 30K, 34K are magnetically attracted to each other, approximating the leaflets LF1, LF2 and maintaining the leaflets in the approximated state.

Figure 14:
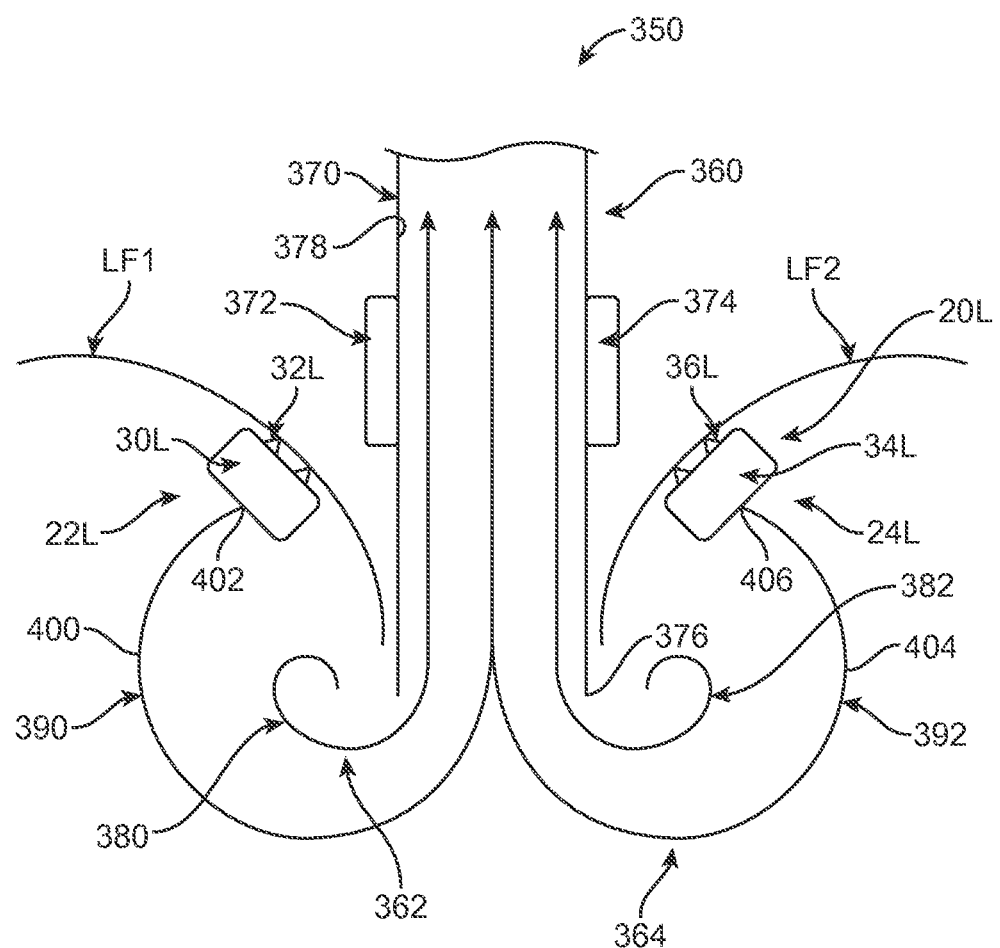
FIG. 14 is a simplified side view of another tissue approximation system and another delivery system in accordance with principles of the present disclosure relative to two tissue segments.

FIG. 14 illustrates, in simplified form, another embodiment tissue approximation system 20L (referenced generally) in accordance with principles of the present disclosure being deployed to the opposing leaflets LF1, LF2 of a mitral valve target site via a delivery system 350. The approximation system 20L includes a first tissue approximation device 22L and a second tissue approximation device 24L. The approximation devices 22L, 24L each include a magnetic component 30L, 34L, respectively, that can have any of the forms described above. In addition, the devices 22L, 24L can each include an attachment mechanism 32L, 36L, respectively, that can assume any of the forms described or implicated by the present disclosure; with the non-limiting example of FIG. 14, the attachment mechanism, such as barbs 32L, 36L. Upon release from corresponding tools of the delivery system 350, the magnetic components 30L, 34L will approximate the tissue segments LF1, LF2. The delivery system 350 can alternatively be useful with any other tissue approximation systems of the present disclosure and is not limited to the particular configuration of FIG. 14.

The delivery system 350 can incorporate various features appropriate for achieving the spatial arrangements of the exemplary mitral valve procedure of FIG. 14 on a minimally invasive basis. For example, in some embodiments, the delivery system 350 includes an outer tube assembly 360, a first tool 362, and a second tool 364. The delivery tools 362, 364 are separately provided but are commonly carried within the outer tube assembly 360. Alternatively, a separate delivery catheter can be provided with each of the tools 362, 364. Regardless, the tools 362, 364 can be manipulated independent of one another in accessing the target site from the same side of the mitral valve (or other anatomical structure of interest).

The outer tube assembly 360 includes a delivery tube or catheter 370 and magnetic bodies 372, 374. The delivery catheter 370 terminates at a distal tip 376 and defines one or more lumens 378 within which portions of the first and second tools 362, 364 are slidably received. The magnetic bodies 372, 374 are assembled to a wall of the catheter 370 in a circumferentially spaced-apart fashion. A longitudinal location of the magnetic bodies 372, 374 relative to the distal tip 376 corresponds with a spatial arrangement of components of the second tool 364, and in particular an expected spatial location of the magnetic components 30L, 34L with operation of the second tool 364 as described below. The magnetic bodies 372, 374 can assume any of the forms described above with respect to the magnetic components of the present disclosure, and are each configured to generate a magnetic pole complementary to that of the corresponding magnetic component 30L, 34L. More particularly, the first magnetic body 372 is formatted in tandem with the magnetic component 30L of the first approximation device 22L such that the first magnetic body 372 and the magnetic component 30L are magnetically attracted to one another when arranged as shown, and the second magnetic body 374 is formatted in tandem with the magnetic component 34L of the second approximation device 24L such that the second magnetic body 374 and the magnetic component 34L are magnetically attracted to one another when arranged as shown. In some embodiments, one or both of the magnetic bodies 372, 374 is an electromagnetic, affording a user the ability to selectively activate and deactivate a magnetic field generated by the magnetic body 372, 374.

The first tool 362 is generally configured for capturing the leaflets LF1, LF2 via a transeptal or transatrial (or similar) approach to the mitral valve target site. The first tool 362 includes a capture device having a variety of forms, and in some embodiments is akin to previous descriptions comprising opposing, first and second arms 380, 382. The first and second arms 380, 382 can assume various forms for capturing or constraining the leaflets LF1, LF2 when deployed from the delivery catheter 370. For example, the arms 380, 382 can be wire-like bodies each configured to self-revert to (e.g., shape memory material), or be directed to (e.g., via pull wire(s) or similar mechanisms), a predetermined shape when exposed distal the delivery catheter 370 appropriate for capturing a respective one of the leaflets LF1, LF2. The arms 380, 382 are shaped to project outwardly and proximally in the deployed state shown, with the first arm 380 extending opposite the second arm 382. Further, the arms 380, 382 readily collapse when located within the delivery catheter 370 for low profile, transcatheter delivery (or other minimally invasive technique) to the target site. Other leaflet-capturing designs are equally acceptable.

The second tool 364 is generally configured for delivering the magnetic components 30L, 34L to the mitral valve target site via a transeptal or transatrial (or similar) approach, and can include a first shaft 390 and a second shaft 392. The shafts 390, 392 can be solid or hollow bodies, and in some embodiments each includes one or more wires formed of a shape memory material. The first shaft 390 includes a distal section 400 terminating at a shaft end 402. The shaft end 402 is configured to selectively maintain the magnetic component 30L (e.g., frictional fit, one more retention mechanism, etc.), with at least the distal section 400 configured to self-revert to a shape appropriate for locating the shaft end 402 (and thus the magnetic component 30L) adjacent the first leaflet LF1 when distally exposed (i.e., the curved shape shown). The second shaft 392 similarly includes a distal section 404 terminating at a shaft end 406 configured to selectively maintain the magnetic component 34L. The distal section 404 of the second shaft 392 is configured to self-revert to the curved shape shown when distally exposed, thus presenting the magnetic component 34L adjacent the second leaflet LF2. The distal sections 400, 404 readily collapse when located within the delivery catheter 370 for low profile, transcatheter delivery (or other minimally invasive technique) to the target site. The second tool 364 can assume a wide variety of other forms, and can include structures or mechanisms not directly implicated by FIG. 14.

During use, the first and second delivery tools 362, 364 are percutaneously delivered to the mitral valve target site via the patient's vasculature, with the arms 380, 382 and the shafts 390, 392 maintained within the delivery catheter 370. The delivery catheter 370 can be routed through the femoral vein, into the right atrium, and then across the septum through a punctured hole by following a guide wire, through an introducer, or by direct navigation. The distal tip 376 is thus directed into left atrium and positioned immediately proximate the mitral valve (e.g., at the inflow side or the outflow side of the mitral valve). The first tool 362 is then deployed from the delivery catheter 370, with the arms 380, 382 being directed toward the pre-determined shapes and spatial orientations as shown. In the deployed state, the first arm 380 generally engages or captures the first leaflet LF1 and the second arm 382 generally engages or captures the second leaflet LF2 (e.g., the arms 380, 382 can initially be deployed in the left ventricle at a location beyond the leaflets LF1, LF2 and then proximally retracted to capture the corresponding leaflet LF1, LF2).

The second tool 364 is then operated to deploy the approximation devices 22L, 24L. The shafts 390, 392 (including the magnetic components 30L, 34L carried thereby) are deployed from the catheter 360, locating the approximation device 30L, 34L in close proximity to the corresponding, captured leaflet LF1, LF2. Upon achieving the arrangement of FIG. 14, a magnetically attractive force or field is established between the first magnetic body 372 and the magnetic component 30L of the first approximation device 22L, and between the second magnetic body 374 and the magnetic component 34L of the second approximation device 24L. Due to the magnetic force, the first approximation device 22L is "pulled" toward the first magnetic body 372, with the attachment mechanism, such as barbs 32L, piercing through the first leaflet LF1 to effectuate attachment of the first approximation device 22L to the first leaflet LF1. The second approximation device 24L similarly becomes attached to the second leaflet LF2 via magnetic attraction with the second magnetic body 374.

Once the approximation devices 22L, 24L are attached to the corresponding leaflet LF1, LF2 (e.g., directly connected to the leaflet LF1, LF2 by an attachment mechanism, indirectly associated via a centrally placed magnetic body as in FIG. 12, etc.), the magnetic components 30L, 34L can then be released from the corresponding shaft 390, 392, and the second tool 364 withdrawn from the patient. Similarly, the arms 380, 382 can be retracted and the first tool 362 withdrawn. Finally, the magnetic coupling between the first magnetic body 372 and the magnetic component 30L of the first approximation device 22L is released, and the magnetic coupling between the second magnetic body 374 and the magnetic component 34L of the second approximation device 24L is released. For example, the delivery catheter 370 can be rotated, moving the magnetic bodies 372, 374 a sufficient distance away from the corresponding magnetic component 30L, 34L to lessen the magnetic coupling or attraction. In other embodiments in which the magnetic bodies 372, 374 are each an electromagnetic, the electrical current to the magnetic bodies 372, 374 is stopped. Regardless, the outer tube assembly 360 can then be removed from the patient. The approximation devices 22L, 24L are magnetically attracted to each other (via magnetic attraction between the corresponding magnetic components 30L, 34L), approximating the leaflets LF1, LF2 and maintaining the leaflets LF1, LF2 in the approximated state.

Figure 15:
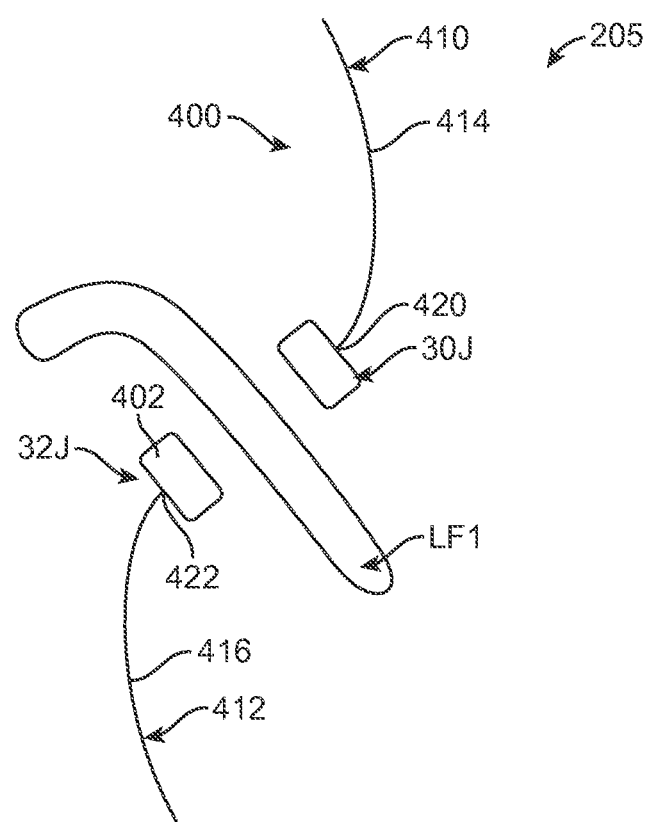
FIG. 15 is a simplified side view of a portion of another tissue approximation device and corresponding delivery system relative to a tissue segment.

Portions of another embodiment approximation system 20J in accordance with principles of the present disclosure are shown, in simplified form, in FIG. 15 as being deployed to a tissue segment, such as one of the leaflets LF1 of a mitral valve target site via a delivery system 400 (referenced generally). The approximation system 20J can be akin to the approximation system 20E (FIG. 7A) described above, and generally includes two approximation devices, with FIG. 15 illustrating a first approximation device 22J (it being understood that the second approximation device can be identical to the first approximation device 22J). The approximation device 22J includes a magnetic component 30J and an attachment mechanism 32J. The magnetic component 30J can have any of the forms described above. The attachment mechanism 32J can also assume a variety of constructions, and with the embodiment of FIG. 15, includes a magnetic body 402.

The delivery system 400 includes a first tool 410 and a second tool 412. The tools 410, 412 can be similar in many respects, each including a catheter (not shown) slidably maintaining a shaft 414, 416, respectively. A distal end 420 of the first shaft 414 is releasably coupled to magnetic component 30J; a distal end 422 of the second shaft 416 is releasably coupled to the magnetic body 402. Finally, the first tool 410 is adapted to deliver the magnetic component 30J to one side of the tissue segment LF1, and the second tool 412 is adapted to deliver the magnetic body 402 to an opposite side of the tissue segment LF1.

For example, in some embodiments where the tissue approximation procedure is performed at a mitral valve leaflet target site, the first tool 410 is manipulated, on a minimally invasive basis, to locate the shaft distal end 420, and thus the magnetic component 30J, adjacent the leaflet LF1 via a transeptal or transatrial approach. Conversely, the second tool 412 is manipulated, on a minimally invasive basis, to locate the shaft distal end 422, and thus the magnetic body 402, adjacent an opposite side of the leaflet LF1 via a transapical or transaortic approach. Once the magnetic component 30J and the magnetic body 402 are sufficiently close, the magnetic component 30J and the magnetic body 402 are magnetically attracted to one another and become secured at opposite sides of the leaflet LF1. The shafts 414, 416 can then be released from the magnetic component 30J and the magnetic body 402, respectively, and withdrawn from the patient.

Systems and methods of the present disclosure can incorporate a number of different features for capturing tissue segments to be approximated on a minimally invasive basis. For example, with non-limiting embodiments directed toward mitral valve leaflet approximation, the leaflet capturing device or devices can be configured to capture and manipulate the mitral valve leaflet chordae as described, for example, in Rothstein, U.S. Publication No. 2012/0277853 the entire teachings of which are incorporated herein by reference.

Figure 16A:
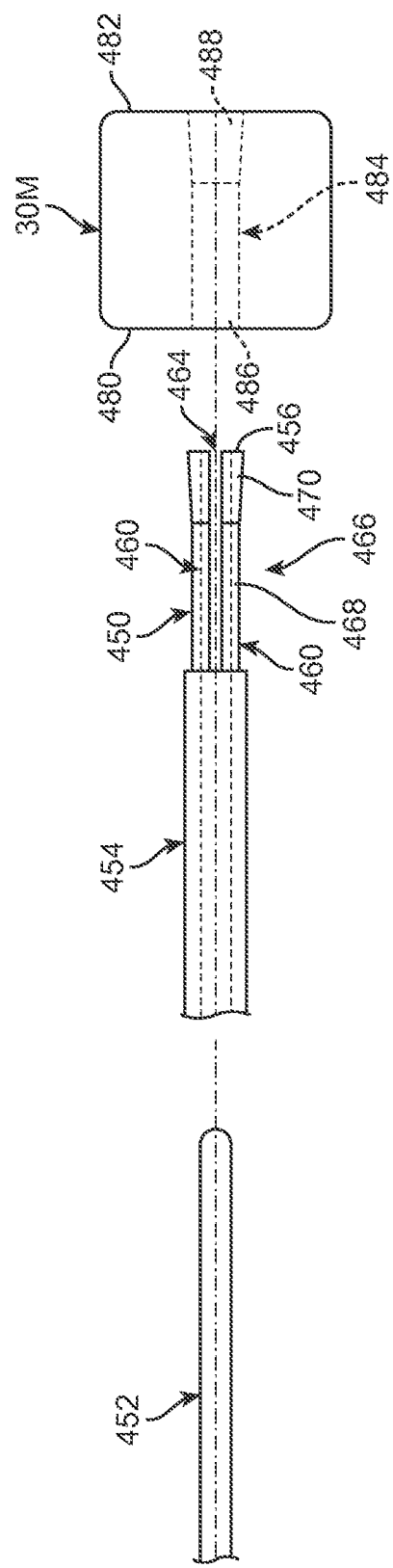
FIG. 16A is a side view illustrating portions of a delivery system and of a magnetic component useful with tissue approximation systems and delivery systems of the present disclosure.
Figure 16B:
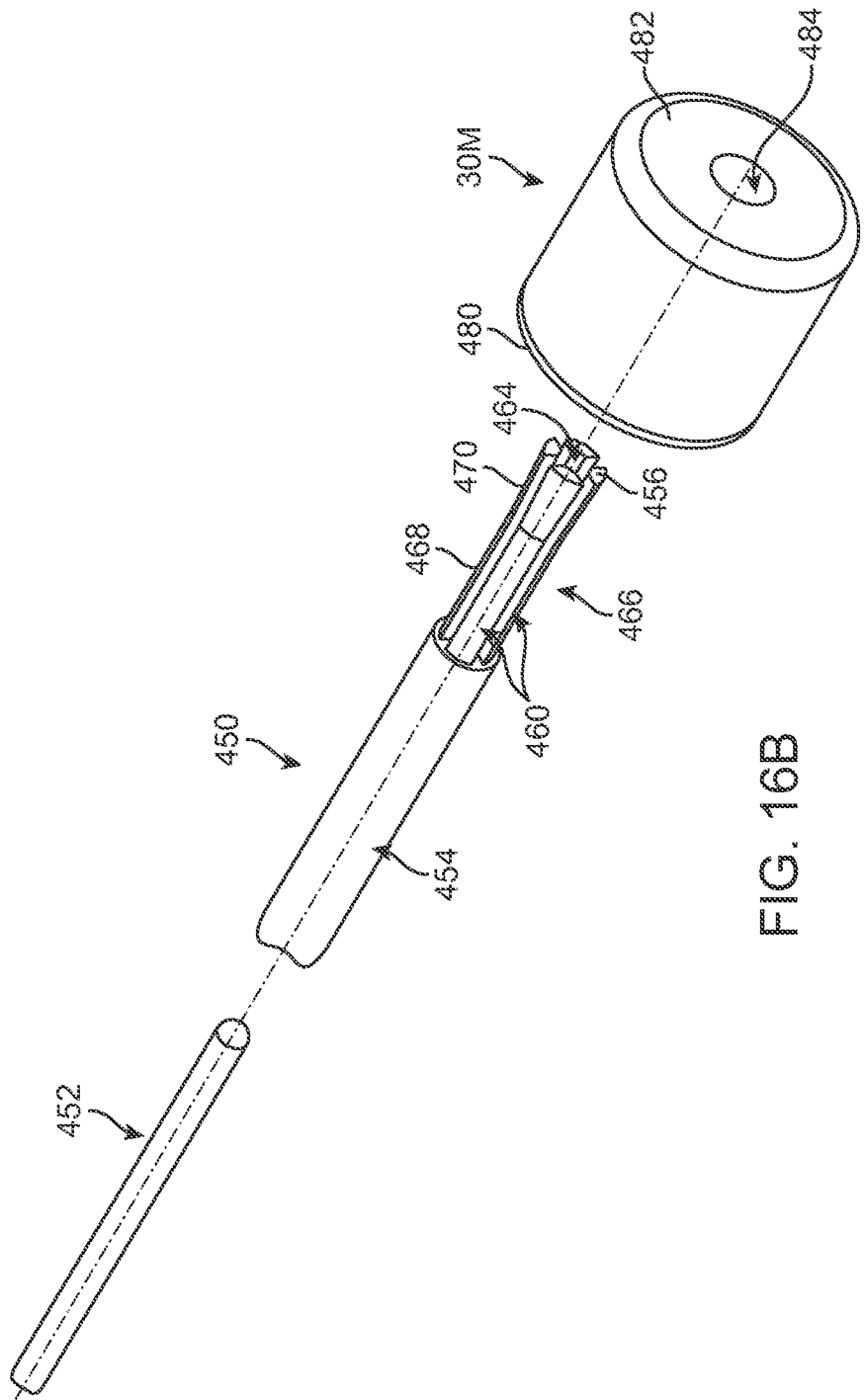
FIG. 16B is a perspective view of the delivery system of FIG. 16A.

In several of the optional embodiments described herein, a magnetic component or magnetic body is releasably coupled to a shaft or wire for delivery to a target site. The present disclosure envisions that this releasable coupling (e.g., once the magnetic component or body is affixed at the target site, the shaft or wire can be uncoupled and removed) can be effectuated in a number of different ways using various structures or mechanisms. One non-limiting, optional example is reflected by FIGS. 16A and 16B that otherwise illustrate a magnetic component 30M in conjunction with components of a delivery system including a shaft 450 and a plug 452. The shaft 450 terminates at a distal end 456 configured to be releasably coupled to the magnetic component 30M. The shaft 450 can include a sleeve 454 supporting two or more legs 460 (e.g., FIGS. 16A and 16B illustrate four of the legs 460). The legs 460 extend distally from the sleeve 454 to the distal end 456 and are separated by a variable spacing 464. That is to say, the shaft 450 is not necessarily a singular, homogenous body, but instead can be collectively generated by the discrete legs 460. In other embodiments, the legs 460 can be more directly connected to one another (e.g., an entirety of the shaft 450 is a tubular body). Regardless, the spacing 464 is sized to slidably receive the plug 452 such that when inserted, the plug 452 prevents the legs 460 from collapsing or deflecting toward one another. As a point of reference, FIGS. 16A and 16B reflect the legs 460 in an expanded condition that is otherwise rigidly maintained by the plug 452 when inserted between the legs 460; at any region of the shaft 450 where the plug 452 is not otherwise present, however, the legs 460 can be collapsed toward one another. Finally, the shaft 450 defines a distal section 466 having a first region 468 and a second region 470. In at least the expanded condition of the shaft 450, an outer diameter of the first region 468 can be substantially uniform whereas the second region 470 defines an increasing outer diameter in distal extension from the first region 468 to the distal end 456.

The magnetic component 30M includes features configured to interface with distal section 466 of the shaft 450. For example, the magnetic component 30M defines opposing, first and second ends 480, 482 and an internal passage 484. A first segment 486 of the internal passage 484 extends from (and is open at) the first end 480, and has a relatively uniform diameter. A second segment 488 of the internal passage 484 extends from the first segment 486 in a direction of the second end 482 and defines an increasing diameter. A size and shape of the internal passage 484 corresponds with the size and shape of the shaft distal section 466 to effectuate releasable attachment between the shaft 450 and the magnetic component 30M. For example, a size or diameter of the internal passage 484 along the first segment 486 approximates a size or diameter of the first region 468 of the shaft distal section 466 (in the expanded condition), and a size or diameter of the internal passage 484 along the second segment 488 approximates a size or diameter of the second region 470 of the shaft distal section 466 (in the expanded condition). However, a diameter of the internal passage 484 at the first end 480 is less than a size or diameter of the shaft distal end 456 in the expanded condition The shaft 450 can be assembled to the magnetic component 30M by withdrawing the plug 452 at least from the distal section 466. The legs 460 can then be collapsed toward one another until an outer diameter of the shaft distal end 456 is less than a diameter of the internal passage 484 at the first end 480. The shaft distal section 466 can then be inserted into the internal passage 484. Once inserted, the plug 452 can be advanced within the distal section 466, forcing the legs 460 to the expanded condition whereby the distal section second region 470 engages surfaces of the magnetic component 30M along the internal passage second segment 488. The plug 452 prevents the legs 460 from collapsing toward one another, thus "locking" the shaft distal section 466 within the internal passage 484 (i.e., were the magnetic component 30M held stationary and a proximal retraction force applied to the shaft 450, the shaft 450 would not disengage from the magnetic component 30M). When a user desires to release the shaft 450 from the magnetic component 30M, the plug 452 is removed. Under conditions where the magnetic component 30M is then held stationary (e.g., is attached to a tissue segment as described herein) and a proximal retraction force applied to the shaft 450, the distal section second region 470 slides proximally along the tapered diameter of the internal passage second segment 488 causing the legs 460 to collapse toward one another. With further proximal retraction, the legs 460 continue to collapse, allowing the distal section 466 to be released from the magnetic component 30M.

It will be understood that the releasable assembly described above is but one approach envisioned by the present disclosure. A number of other releasable attachment constructions are equally acceptable.

Figure 17:
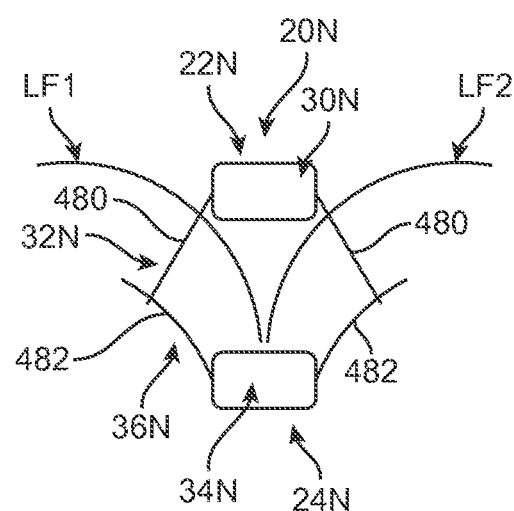
FIG. 17 is a simplified side view of another tissue approximation system in accordance with principles of the present disclosure as applied to two tissue segments.

Portions of another tissue approximation system 20N and exemplary method of use are shown in simplified form in FIG. 17. As with previous embodiments, the system 20N comprises first and second tissue approximation devices 22N, 24N. The first tissue approximation device 22N includes a magnetic component 30N and an attachment mechanism 32N; the second tissue approximation device 24N includes a magnetic component 34N and an attachment mechanism 36N. The magnetic components 30N, 34N can have any of the forms described above. The attachment mechanisms 32N, 36N can be identical in some embodiments, and are generally configured for connecting the corresponding magnetic component 30N, 34N with both of the tissue segments LF1, LF2. That is to say, unlike some previous embodiments in which each tissue approximation device is affixed to a single one of the two tissue segments to be approximated, with the embodiments of FIG. 17, both tissue approximation devices 22N, 24N are attached to both of the tissue segments LF1, LF2.

The attachment mechanisms 32N, 36N can assume various forms appropriate for attachment to both of the tissue segments LF1, LF2. For example, in the one non-limiting embodiment shown, the attachment mechanism 32N, 36N can each include two (or more) connectors 480, 482 in form of pins, wires, sutures, etc. One or more of the connectors 480, 482 are configured to piece through a thickness of a corresponding one of the tissue segments LF1, LF2. In some embodiments, the connectors 480 of the first tissue approximation device 22N are configured to lock or mate with a corresponding one of the connectors 482 of the second tissue approximation device 24N. Regardless, upon final deployment, the tissue approximation devices 22N, 24N are robustly attached to both of the tissue segments LF1, LF2, with magnetic attraction between the magnetic components 30N, 34N drawing the tissue approximation devices 22N, 24N toward one another so as to sandwich, and thus approximate, portions of the tissue segments LF1, LF2 there between.

Figure 18:
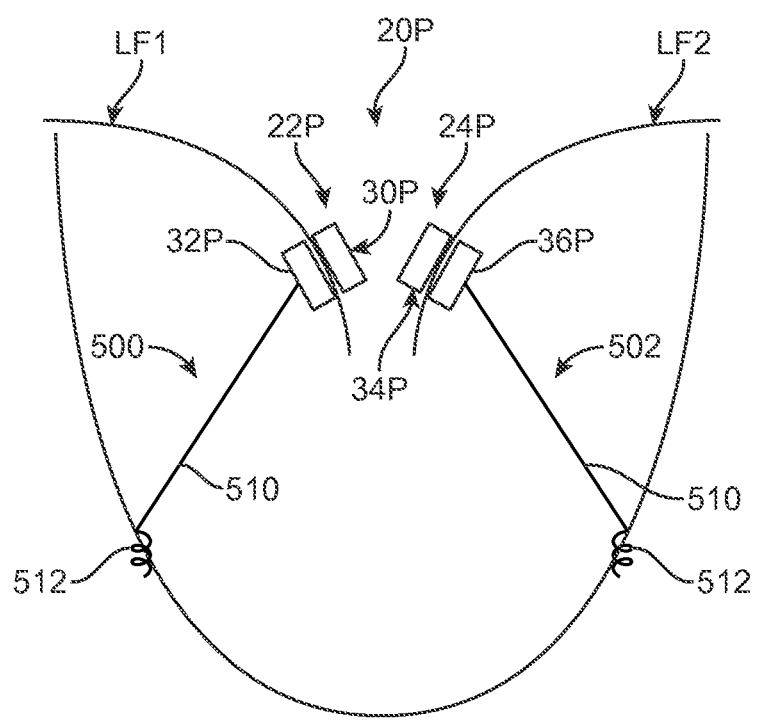
FIG. 18 is a simplified side view of another embodiment tissue approximation system in accordance with principles of the present disclosure as applied to two tissue segments and other anatomy of a target site.

The tissue approximation systems of the present disclosure can be configured to affect an anatomy of the target site in addition to approximating targeted tissue site. For example, FIG. 18 illustrates portions of another embodiment tissue approximation system 20P in simplified form in performing a corresponding, exemplary method of use. The system 20P includes first and second tissue approximation devices 22P, 24P. The first approximation device 22P includes a magnetic component 30P, an attachment mechanism 32P, and a remodeling unit 500. The second approximation device 24P includes a magnetic component 34P, an attachment mechanism 36P, and a remodeling unit 502. The magnetic components 30P, 34P can assume any of the forms described above, as can the attachment mechanisms 32P, 36P. For example, the attachment mechanisms 32P, 36P can each include a magnetic body appropriate for attaching the corresponding magnetic component 30P, 34P to one of the tissue segments LF1, LF2, although any of the other attachment mechanism formats described above (e.g., clips, barbs, rivets, etc.) are equally acceptable. Regardless, the remodeling units 500, 502 can be highly similar to one another, and are generally configured to interface with anatomy of the target site apart from the tissue segments LF1, LF2 in a desired fashion.

For example, in some embodiments, the system 20N is useful in remodeling an anatomy of the mitral valve (in addition to approximating the mitral valve leaflets LF1, LF2). With this in mind, the remodeling units 500, 502 can each include a tether 510 and an anchor 512. The tether 510 can be a flexible body (e.g., suture, wire, etc.) that is optionally substantially inextensible. The tether 510 is attached to and extends from the corresponding attachment mechanism 32P, 36P (or other components of the corresponding tissue approximation device 22P, 24P) and terminates at the anchor 512. The anchor 512, in turn, is configured to be implanted or embedded into tissue of the target site (e.g., a tissue screw as is known in the art). FIG. 18 reflects that upon final deployment, the tissue approximation devices 22P, 24P approximate the leaflets LF1, LF2, and maintain the leaflets LF1, LF2 in the approximated state, due to magnetic attraction between the magnetic components 30P, 34P. In addition, the remodeling units 500, 502 effectuate ventricular remodeling, with the tethers 510 essentially serving as additional chordae for the leaflets LF1, LF2. The remodeling units 500, 502 can assume a wide variety of other forms configured to effectuate desired remodeling of a particular target site.

Figure 19:
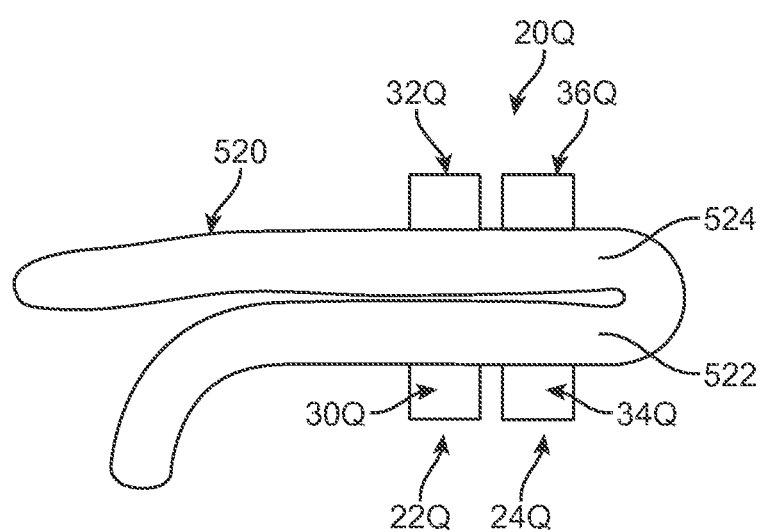
FIG. 19 is a simplified side view of another tissue approximation system in accordance with principles of the present disclosure as applied to a tissue body formed to define two tissue segments.

While some embodiments of the present disclosure have been described as approximating two (or more) discrete tissue segments, in other embodiments, the tissue approximation system can be applied to a singular tissue body. For example, FIG. 19 illustrates, in simplified form, another embodiment tissue approximation system 20Q applied to a tissue body 520. The system 20Q can assume any of the forms described herein, and includes first and second tissue approximation devices 22Q, 24Q each including a magnetic component 30Q, 34Q and an attachment mechanism 32Q, 36Q. With the non-limiting example shown, the attachment mechanisms 32Q, 36Q each include or comprise a magnetic body, although any other attachment mechanism described elsewhere is equally acceptable. Regardless, with the methodology implicated by FIG. 19, the tissue body 520 is folded on to itself and then secured in the folded state by the approximation system 20Q. As a point of reference, in some instances it may be desirable to plicate or shorten a length (or other dimension) of a particular anatomical feature (e.g., a leaflet). Once folded, the tissue body 520 effectively defines two tissue segments 522, 524, and the tissue approximation system 20Q operates to approximate the tissue segments 522, 524, and to maintain the tissue segments 522, 524 in the approximated state.

FIG. 20 illustrates a tissue approximation system 20R as applied to overlapping tissue segments (e.g. heart valve leaflets) LF1, LF2 with the tissue segments LF1, LF2 having been first arranged in an overlapping manner. The system 20R includes first and second approximation devices 22R, 24R. The first device 22R includes at least one magnetic component 30R and an attachment mechanism 32R. The second device 24R can be highly similar to the first device 22R, optionally identical, and also includes at least one magnetic component 34R and an attachment mechanism 36R. As discussed with respect to prior embodiments, the attachment mechanisms 32R, 36R can assume a variety of forms and are each configured to couple or otherwise spatially affix the corresponding magnetic component 30R, 34R relative to a respective one of the tissue segments LF1, LF2. Upon connection to the tissue segments LF1, LF2, the magnetic components 30R, 34R are arranged in a complementary fashion such that the associated magnetic field(s) attracts the magnetic components 30R, 34R (and thus the tissue segments LF1, LF2) toward one another (represented by arrows). Due to this magnetic force or attraction, as discussed above with respect to prior embodiments, the system 20R approximates the tissue segments LF1, LF2 and maintains the so-approximated tissue segments LF1, LF2 in the approximated state. The tissue approximation system 20R can be delivered with delivery systems and methods discussed herein.

Systems and methods of the present disclosure provide a marked improvement over previous designs. Tissue approximation can be accomplished on a minimally invasive basis via a system including complementary magnetic components that produce a magnetic field that acts to maintain two or more tissue approximation components in a desired positional relationship.

Although the present disclosure has been described with reference to preferred embodiments, workers skilled in the art will recognize that changes can be made in form and detail without departing from the spirit and scope of the present disclosure.

What is claimed is:

1. A system for approximation of two heart valve leaflets, the system comprising:
    a first approximation device including a first magnetic component and a first leaflet attachment mechanism, the first leaflet attachment mechanism having first and second jaws secured to a base, wherein the first magnetic component is mounted to an outer surface of the first leaflet attachment mechanism; and
    a second approximation device including a second magnetic component and a second leaflet attachment mechanism, the second magnetic component being mounted to an outer surface of the second leaflet attachment mechanism;
    wherein the first and second leaflet attachment mechanisms are each configured to effectuate attachment of the corresponding device to one heart valve leaflet;
    wherein the magnetic components have a complementary configuration such that the first magnetic component is magnetically attracted to the second magnetic component;
    further wherein the first and second jaws are pivotally connected with respect to the base.

2. The system of claim 1, wherein at least one of the first and second leaflet attachment mechanisms includes a component selected from the group consisting of: clip and a clamp.

3. The system of claim 1, wherein at least one of the first and second approximation devices comprises one or more friction enhancing features selected from the group consisting of: prong, winding, band, barb, bump, groove and channel.

4. The system of claim 1, wherein at least a portion of at least one approximation device comprises one or more friction enhancing features selected from the group consisting of: a rough surface, pad, covering and coating.

5. The system of claim 1, wherein the second approximation device includes a magnetic base; wherein the first magnetic component and the magnetic base are supported relative to opposite sides of a first heart valve leaflet.

6. The system of claim 1, further comprising a connection device connecting the first and second approximation devices.

7. The system of claim 6, wherein the connection device comprises at least one tether selected from the group consisting of: suture, wire, string and a combination thereof.

8. The system of claim 1, wherein the first and second jaws are biased in a closed position.

9. The system of claim 1, wherein the first attachment mechanism includes a first side wall, a second side wall and the base interconnecting the first and second side walls; wherein the first magnetic component is mounted to the second side wall.

* * * * *